US010517980B2

(12) United States Patent
Kim et al.

(10) Patent No.: US 10,517,980 B2
(45) Date of Patent: Dec. 31, 2019

(54) COMPACT AIR CLEANER USING UV LED AND PHOTOCATALYTIC FILTER

(71) Applicant: SEOUL VIOSYS CO., LTD., Gyeonggi-do (KR)

(72) Inventors: Jong Rack Kim, Ansan-si (KR); Jae Seon Yi, Ansan-si (KR); Ik Hwan Ko, Ansan-si (KR); Sang Hwan Byun, Ansan-si (KR); Sang Cheol Shin, Ansan-si (KR); Ji Won Kim, Ansan-si (KR); Seong Min Lee, Ansan-si (KR); Jae Hak Jeong, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 51 days.

(21) Appl. No.: 15/525,045

(22) PCT Filed: Nov. 5, 2015

(86) PCT No.: PCT/KR2015/011867
§ 371 (c)(1),
(2) Date: May 5, 2017

(87) PCT Pub. No.: WO2016/072774
PCT Pub. Date: May 12, 2016

(65) Prior Publication Data
US 2017/0326264 A1 Nov. 16, 2017

(30) Foreign Application Priority Data

Nov. 6, 2014 (KR) .......................... 10-2014-0153955
Nov. 6, 2014 (KR) .......................... 10-2014-0153956
(Continued)

(51) Int. Cl.
*A61L 9/20* (2006.01)
*B01D 53/04* (2006.01)
(Continued)

(52) U.S. Cl.
CPC ................. *A61L 9/20* (2013.01); *A61L 9/205* (2013.01); *B01D 53/04* (2013.01); *B01D 53/86* (2013.01);
(Continued)

(58) Field of Classification Search
None
See application file for complete search history.

(56) References Cited

U.S. PATENT DOCUMENTS

2006/0034737 A1  2/2006  Beam et al.
2006/0159598 A1* 7/2006  Wu .......................... A61L 9/205
                                                    422/186.3
(Continued)

FOREIGN PATENT DOCUMENTS

CN        2747221 Y    12/2005
CN      101598268 A    12/2005
(Continued)

OTHER PUBLICATIONS

International Search Report and Written Opinion for PCT/KR2015/011867, filed Nov. 5, 2015, Applicant: Seoul Viosys Co., Ltd., dated Feb. 23, 2016, ISA/KR, 16 pages.
(Continued)

*Primary Examiner* — Kishor Mayekar
(74) *Attorney, Agent, or Firm* — Perkins Coie LLP

(57) ABSTRACT

An air cleaner is provided to include a photocatalytic UV LED (57) installed on an UV LED substrate (55), and a photocatalytic filter installed on a surface facing the photocatalytic UV LED while being spaced apart from the UV LED substrate. The photocatalytic filter has a structure in which a photocatalytic material is coated on a base in which a plurality of cells (83) defining an air flow path in a direction toward the photocatalytic UV LED are arranged in parallel adjacent to each other.

21 Claims, 16 Drawing Sheets

(30) Foreign Application Priority Data

| Nov. 6, 2014 | (KR) | ........................ 10-2014-0153957 |
| Nov. 6, 2014 | (KR) | ........................ 10-2014-0153958 |
| Nov. 6, 2014 | (KR) | ........................ 10-2014-0153959 |
| Nov. 6, 2014 | (KR) | ........................ 10-2014-0153960 |
| Dec. 4, 2014 | (KR) | ........................ 10-2014-0173020 |

(51) Int. Cl.
- *B01D 53/88* (2006.01)
- *B01D 53/86* (2006.01)
- *B01D 53/58* (2006.01)
- *B01D 53/72* (2006.01)
- *A61L 9/014* (2006.01)

(52) U.S. Cl.
CPC ............ *B01D 53/885* (2013.01); *A61L 9/014* (2013.01); *A61L 2209/14* (2013.01); *B01D 53/0415* (2013.01); *B01D 53/58* (2013.01); *B01D 53/72* (2013.01); *B01D 2253/102* (2013.01); *B01D 2255/20707* (2013.01); *B01D 2255/802* (2013.01); *B01D 2257/406* (2013.01); *B01D 2257/70* (2013.01); *B01D 2257/90* (2013.01); *B01D 2258/06* (2013.01); *B01D 2259/41* (2013.01); *B01D 2259/804* (2013.01)

(56) References Cited

U.S. PATENT DOCUMENTS

| 2010/0209294 A1* | 8/2010 | Owen ..................... A61L 9/205 422/24 |
| 2010/0209312 A1* | 8/2010 | Pastor ..................... A61L 9/205 422/186.3 |
| 2011/0033346 A1* | 2/2011 | Bohlen ................... A61L 9/205 422/186.3 |
| 2011/0048232 A1 | 3/2011 | Jocelin et al. |
| 2011/0100221 A1 | 5/2011 | Wu |
| 2012/0230876 A1 | 9/2012 | Chan et al. |
| 2013/0047857 A1 | 2/2013 | Bohlen |
| 2013/0052090 A1 | 2/2013 | Bohlen |
| 2015/0037217 A1* | 2/2015 | Park ..................... F24F 3/1603 422/121 |
| 2015/0044101 A1* | 2/2015 | Koo ..................... F24F 3/1603 422/121 |

FOREIGN PATENT DOCUMENTS

| CN | 102015064 A | 4/2011 |
| CN | 102962131 A | 3/2013 |
| CN | 204730343 U | 10/2015 |
| JP | H08-224292 A | 9/1996 |
| JP | 20007-209725 A * | 8/2007 |
| WO | 2014022355 A1 | 2/2014 |

OTHER PUBLICATIONS

English translation of Chinese Office Action received in related Chinese Patent Application dated Jan. 17, 2019 (2 pages).

"A Practical Technology of Porous Ceramic" Published in Chinese on Mar. 2006 by China Building Materials Press, and English translation of cited Section and Table attached, (total 6 pages). Cited in Chinese Office Action dated Jan. 17, 2019.

First Office Action dated Aug. 2, 2018 in Chinese Patent Application No. 201510047073.0, 6 pages, English translation.

English translation of Chinese Office Action received in related Chinese Patent Application dated Dec. 27, 2018 (1 page).

English translation of Chinese Office Action received in related Chinese Patent Application No. 201510047562.6 dated Apr. 3, 2019 (2 pages).

English translation of Japanese Office Action received in related Japanese Patent Application No. 2017-523913 dated Oct. 16, 2019 (4 pages).

* cited by examiner

[Fig. 1]
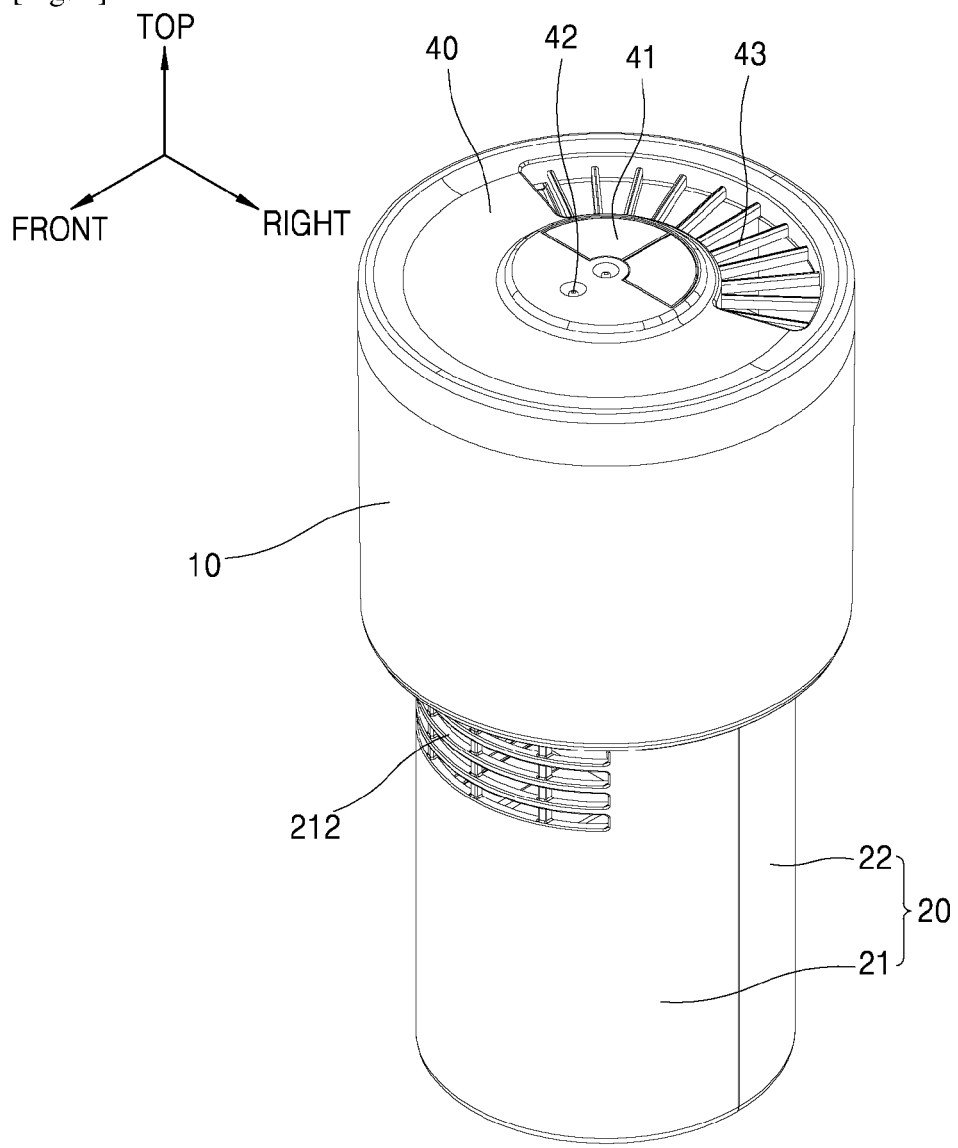

[Fig. 2]
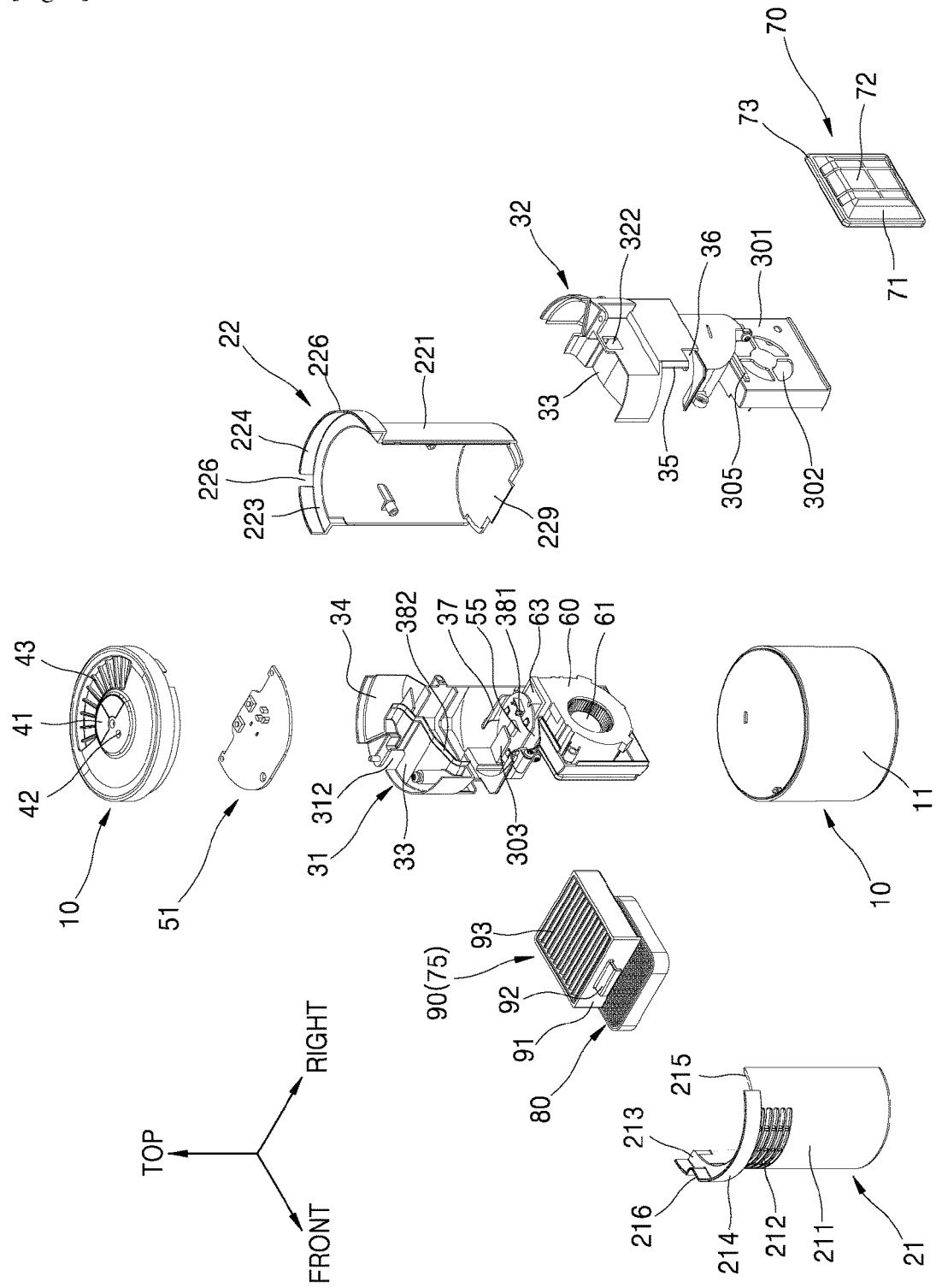

[Fig. 3]
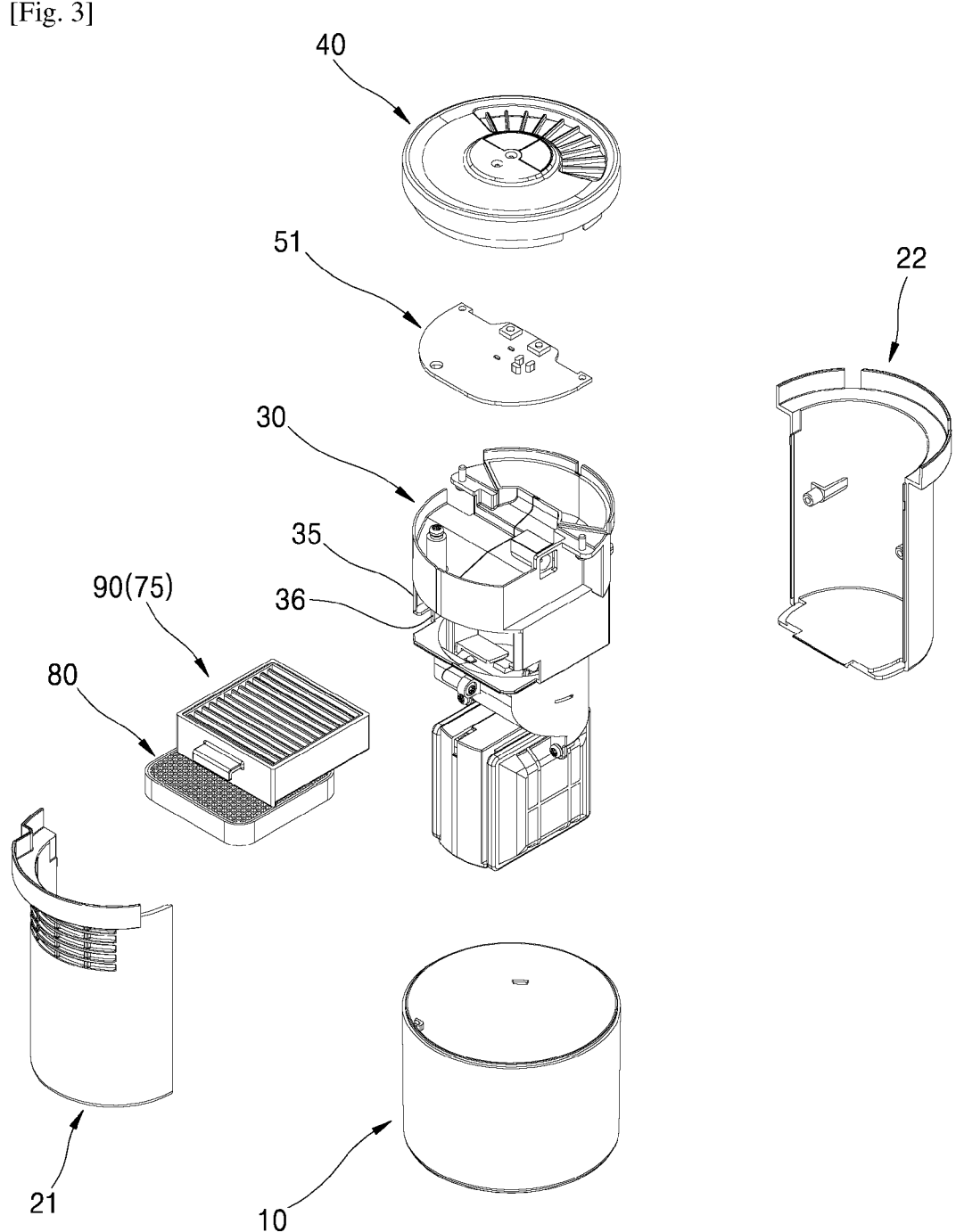

[Fig. 4]
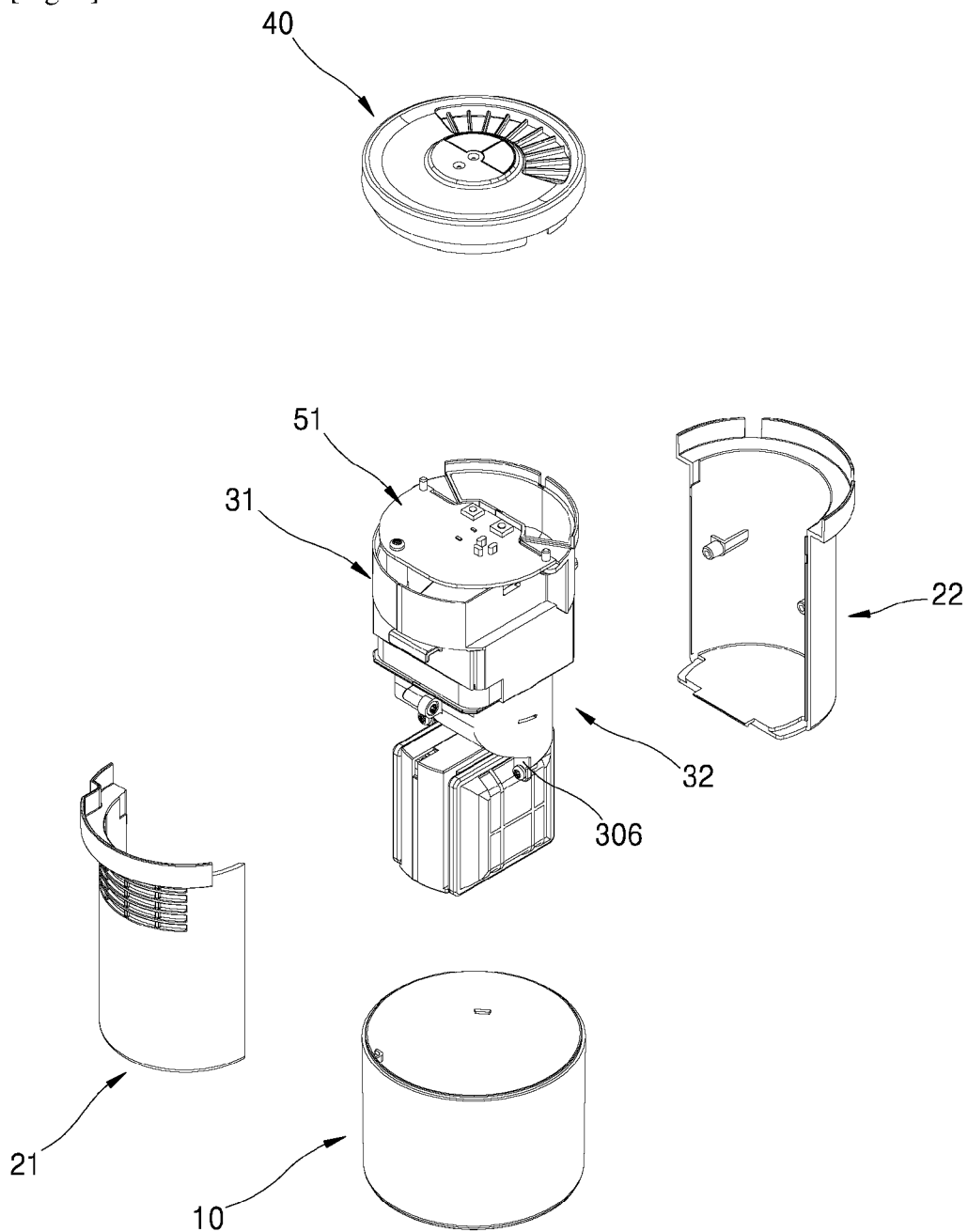

[Fig. 5]
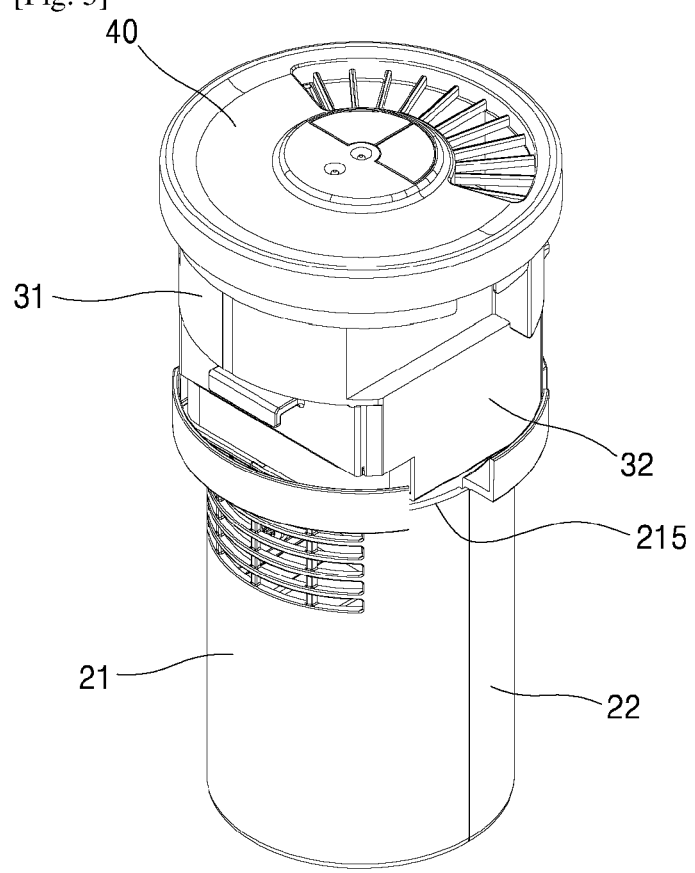
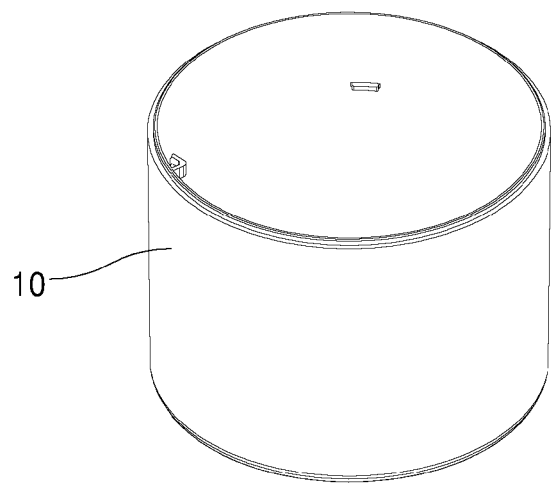

[Fig. 6]
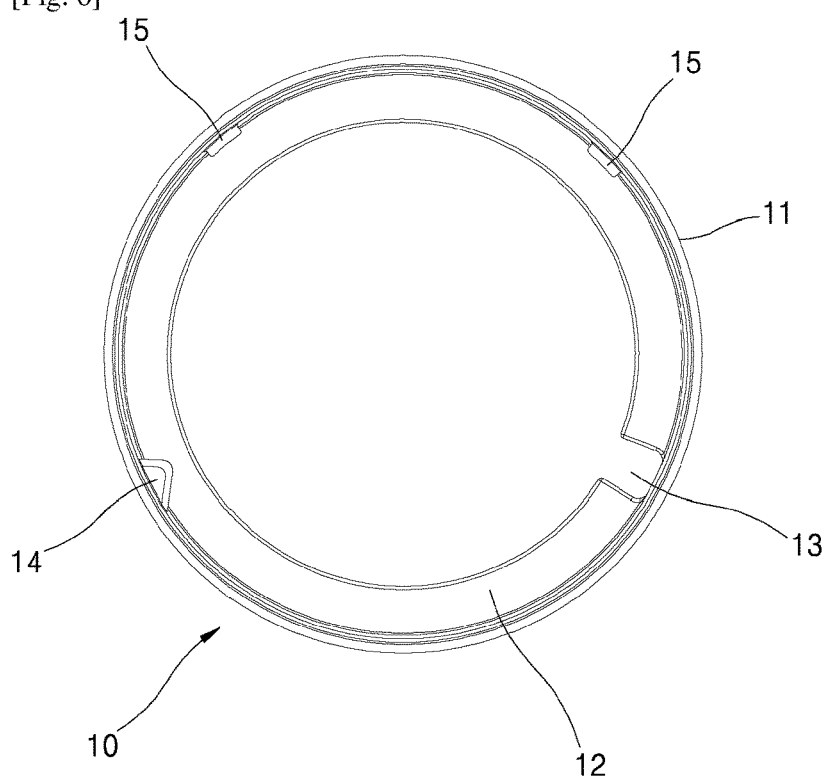
[Fig. 7]
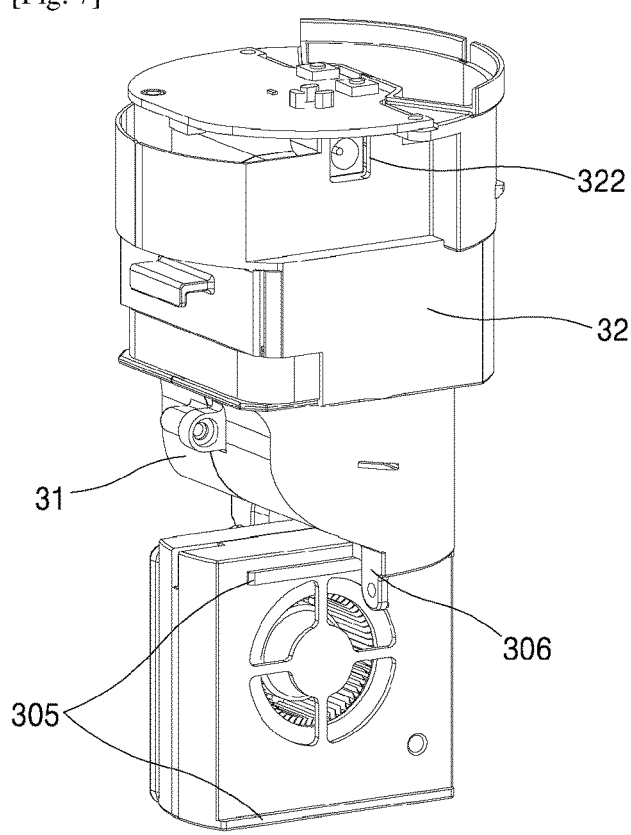

[Fig. 8]
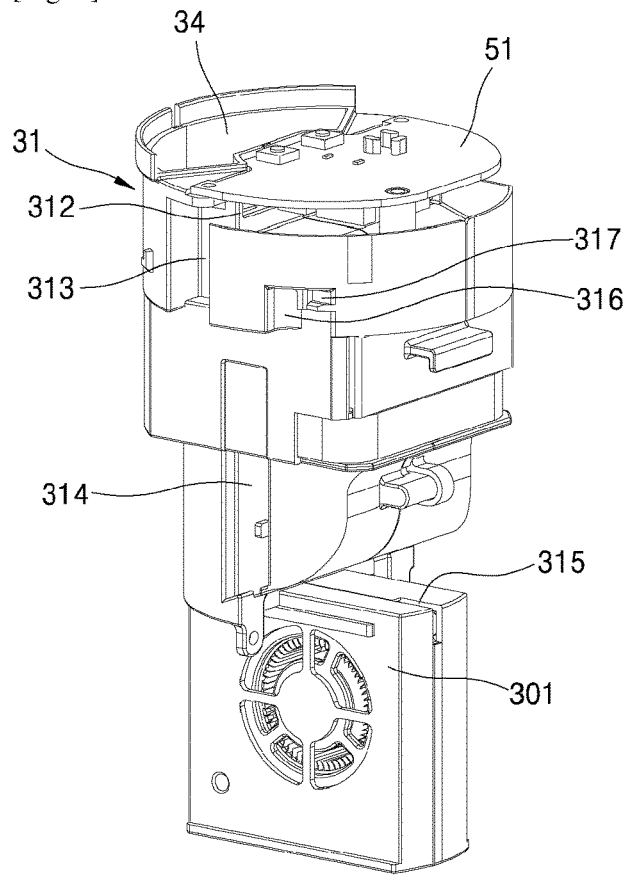
[Fig. 9]
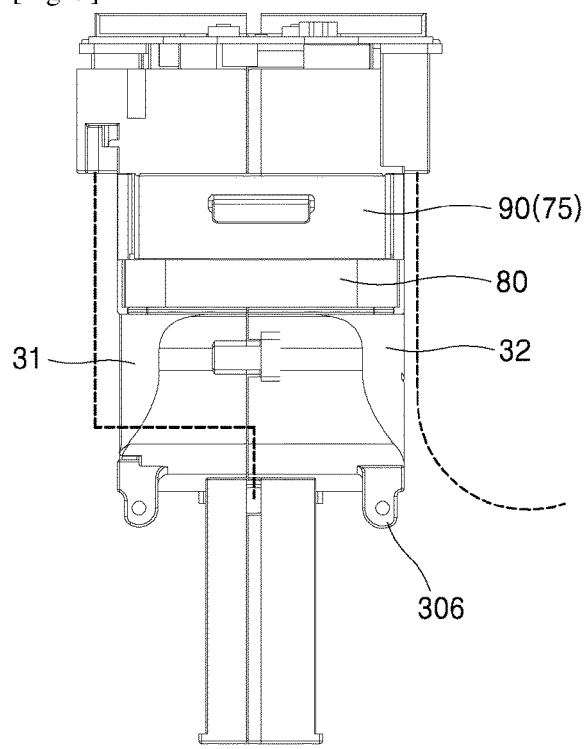

[Fig. 10]
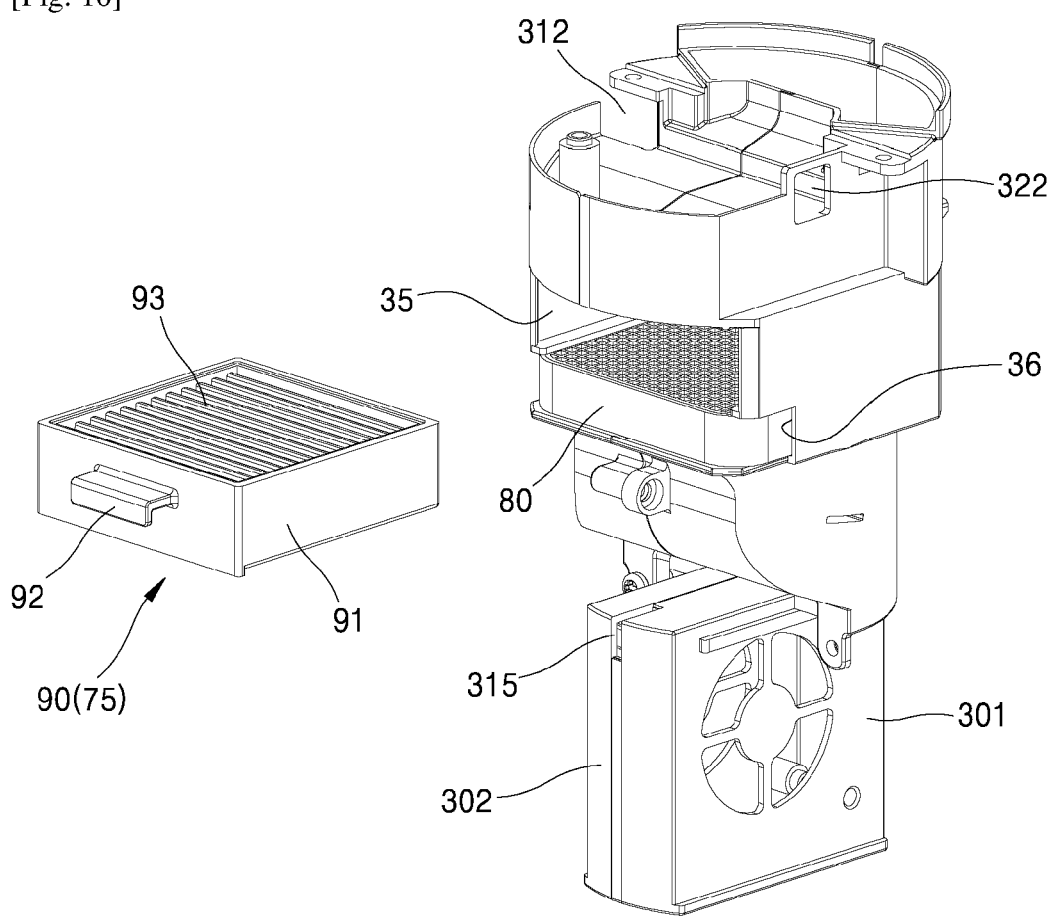

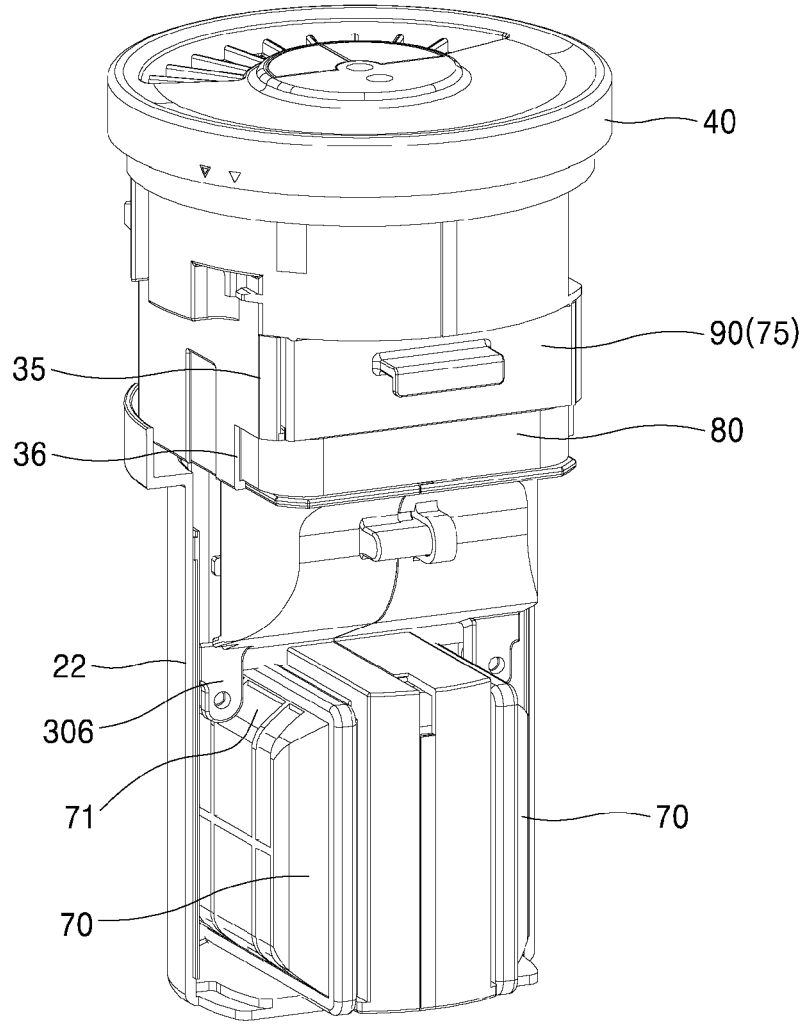
[Fig. 11]

[Fig. 12]
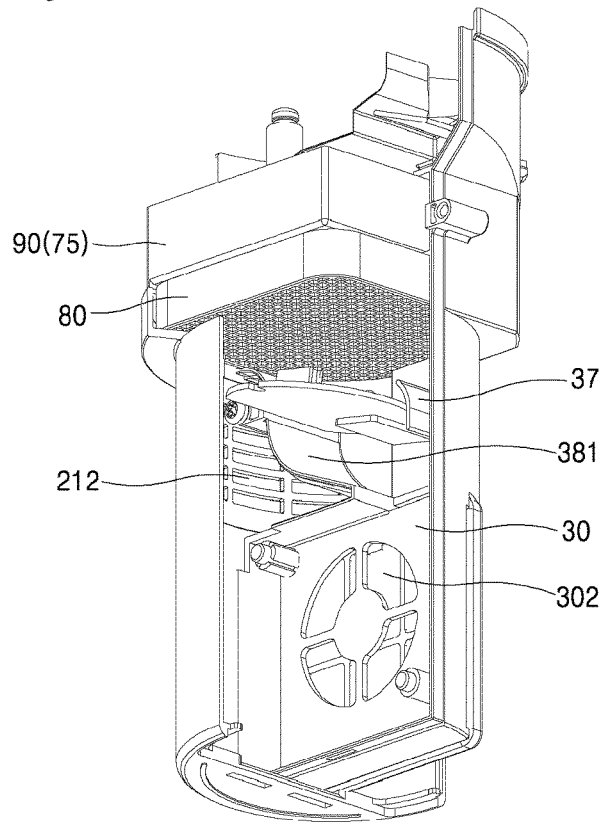
[Fig. 13]
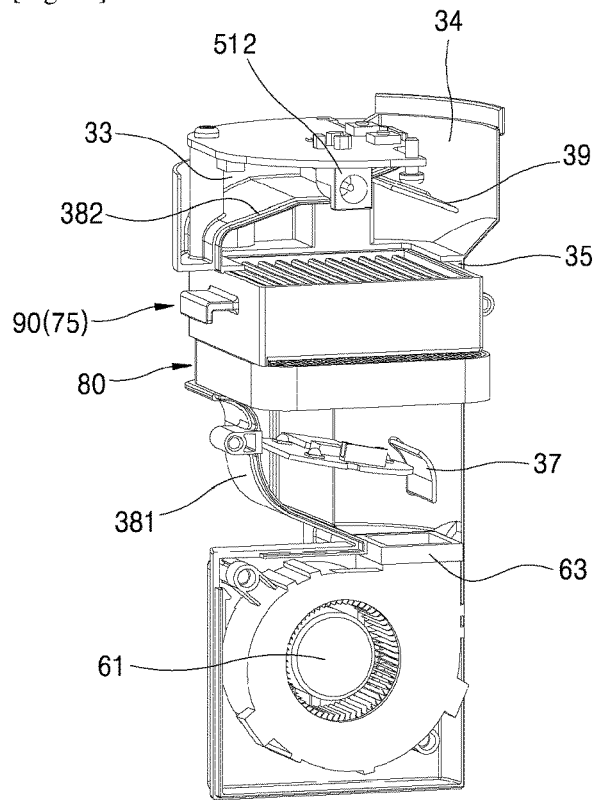

[Fig. 14]
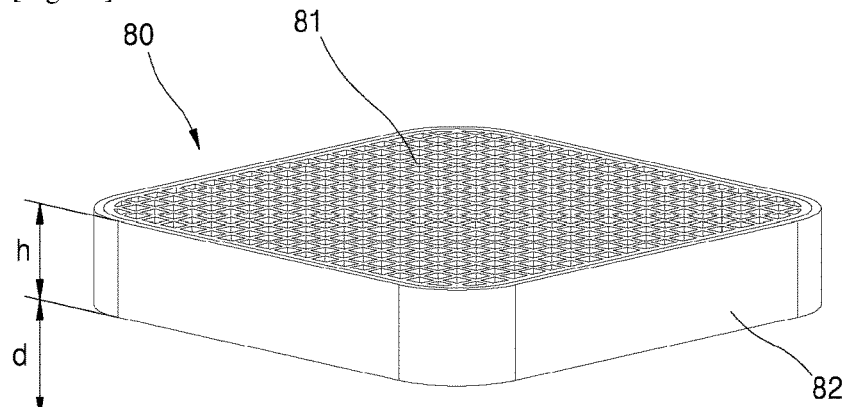
[Fig. 15]
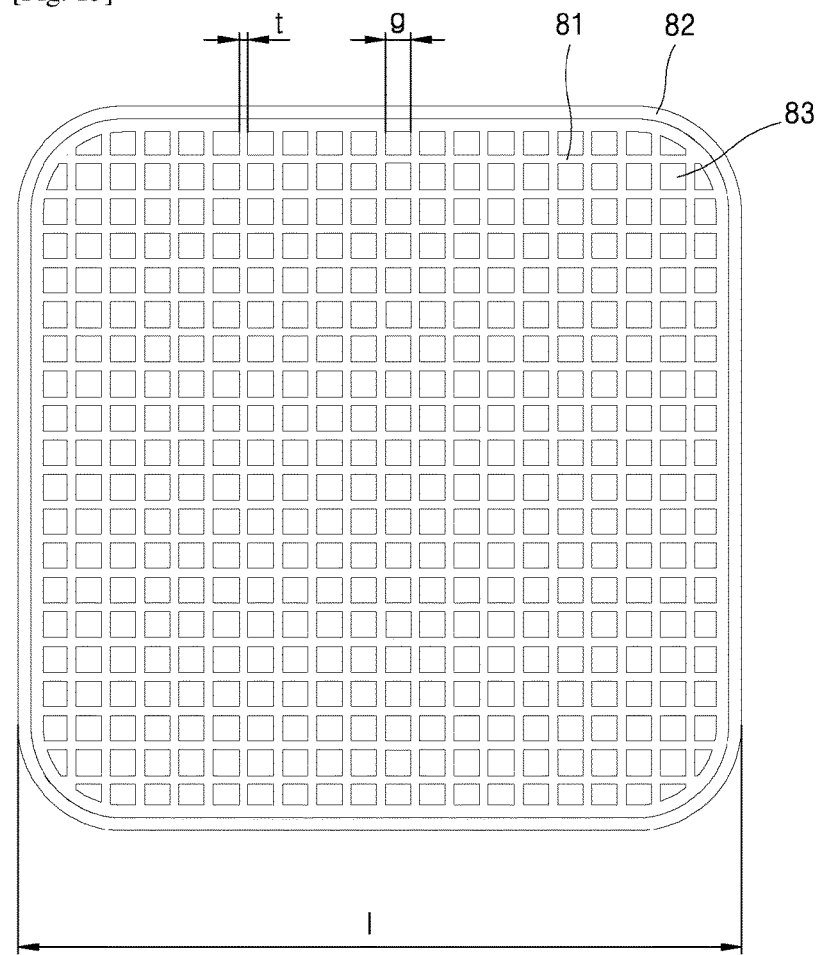

[Fig. 16]
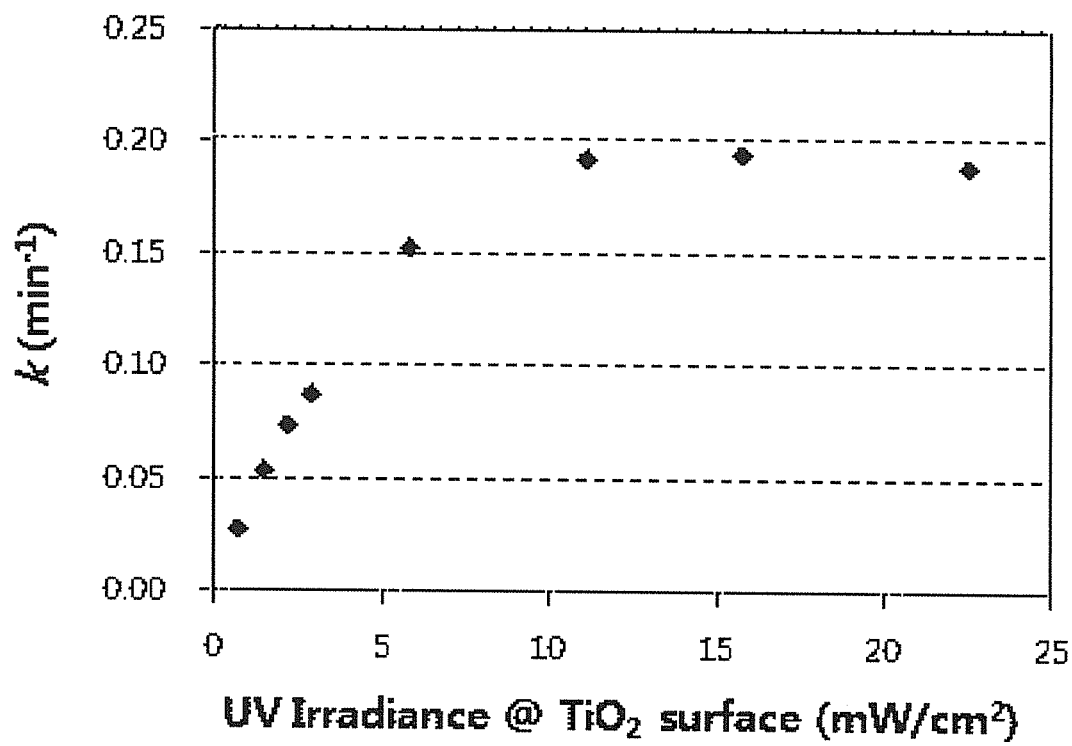
[Fig. 17]
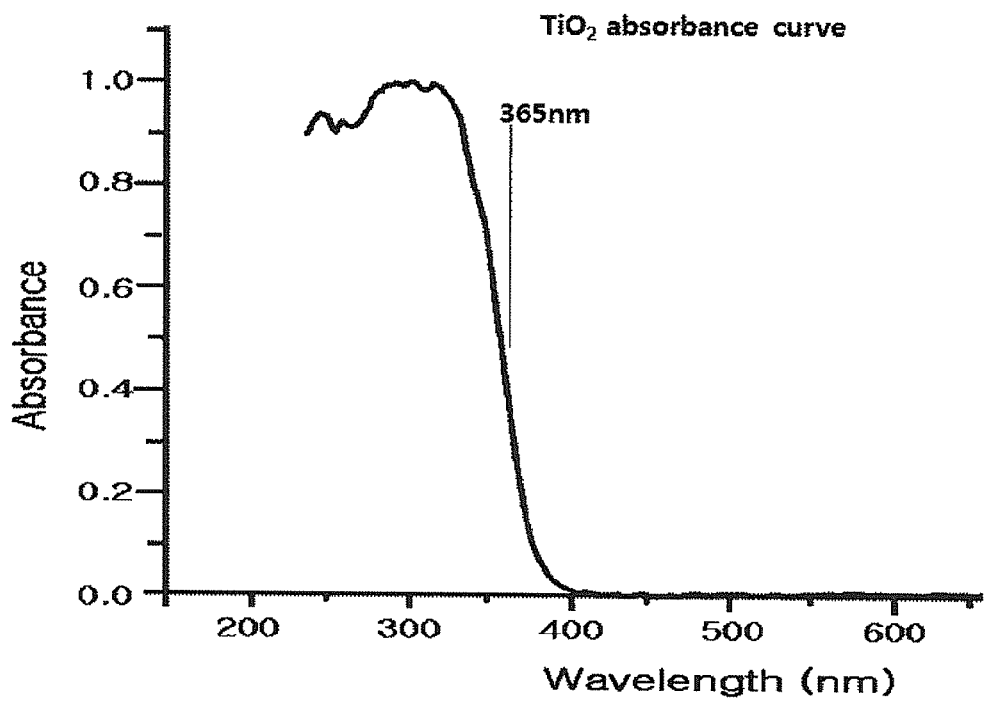

[Fig. 18]
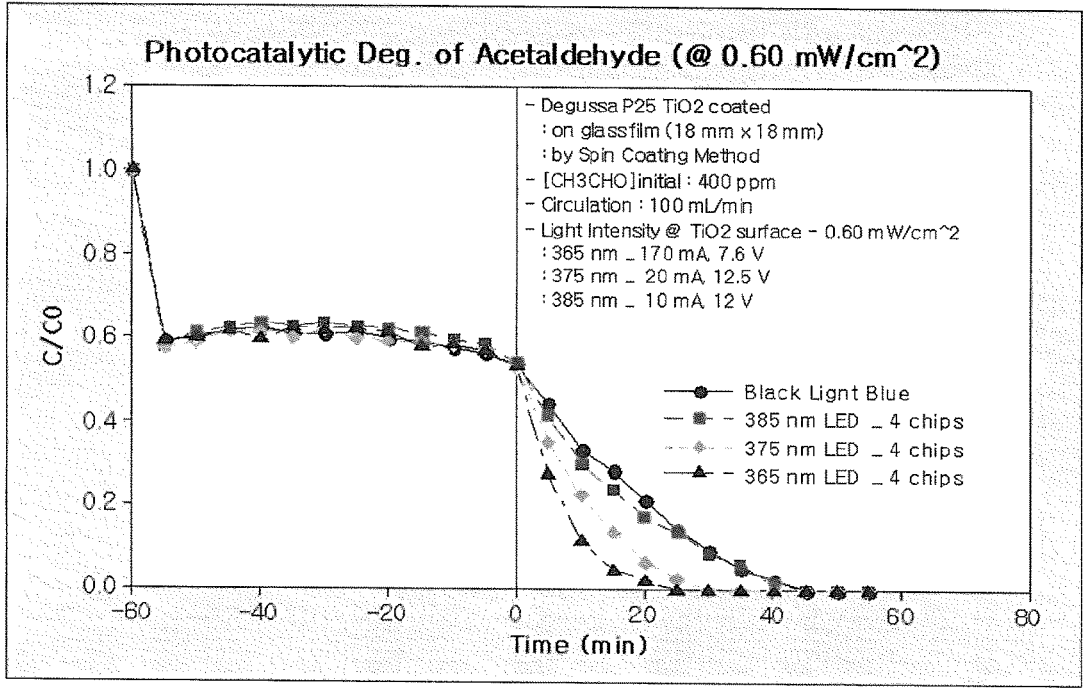
[Fig. 19]
- Experiment Conditions
① 1 m³ Chamber (A)
② Target gas : Acetaldehyde ($CH_3CHO$), 10 ppm
③ RS-PR1 (Flow rate : High @ 3.5 CFM, Abg. Irradiance : 15 mW/cm²)
④ $TiO_2$ : ceramic (100 cpsi), 5T (1.6 g loading) vs. 8.5T (2.6 g loading)
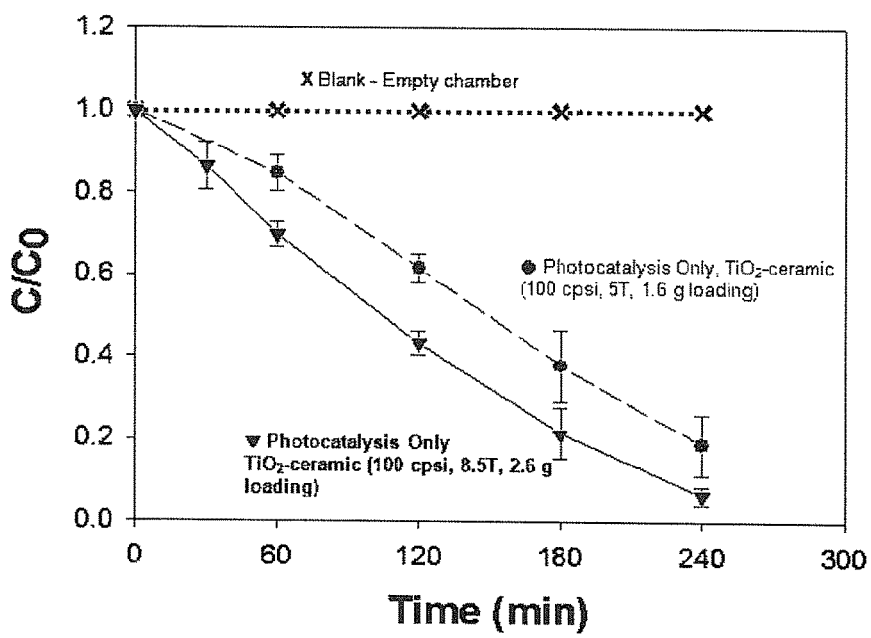

[Fig. 20]
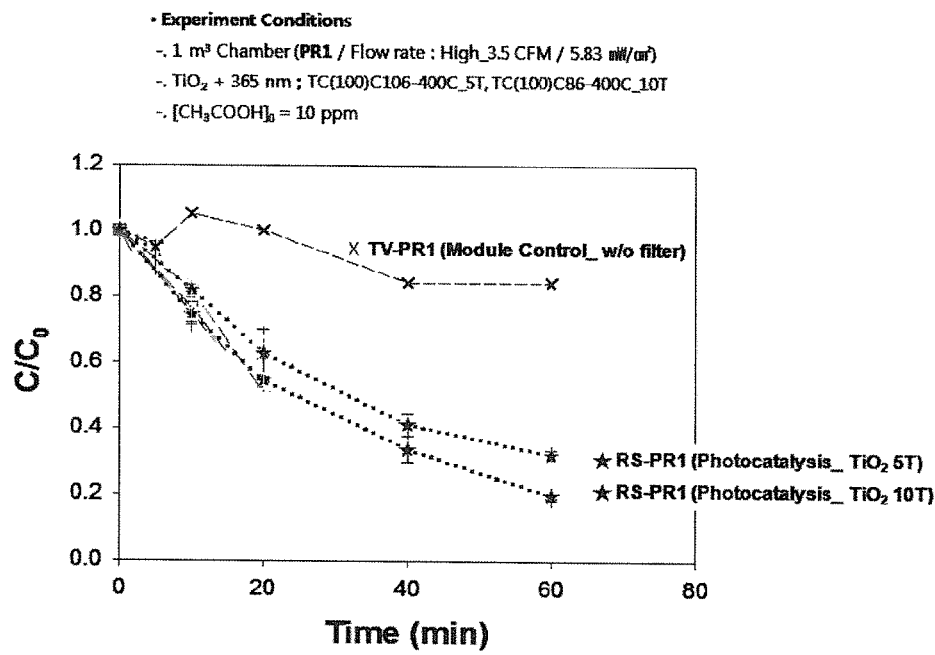
[Fig. 21]
DEODORIZATION PERFORMANCE FOR EACH TEMPERATURE DURING LOADING 2 g OF PHOTOCATALYST IN 27 L CONTAINER
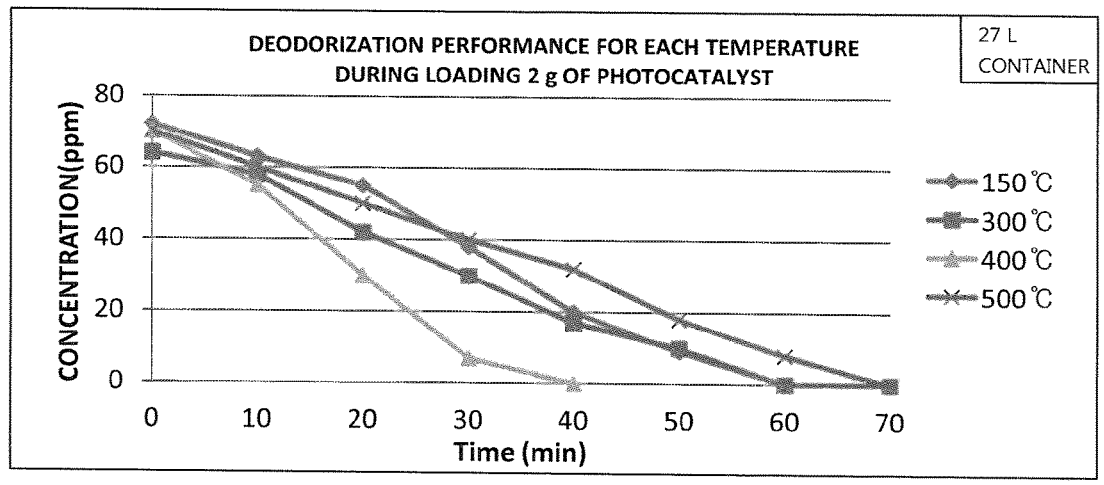

[Fig. 22]
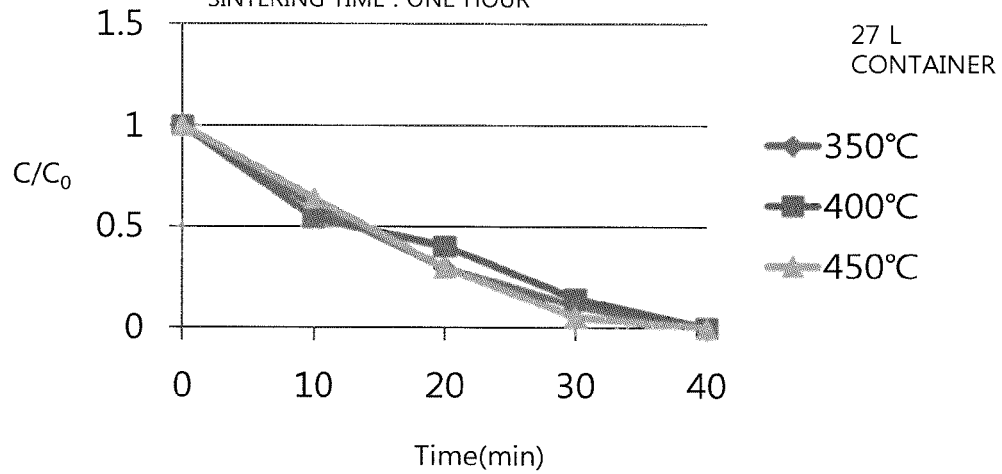
[Fig. 23]
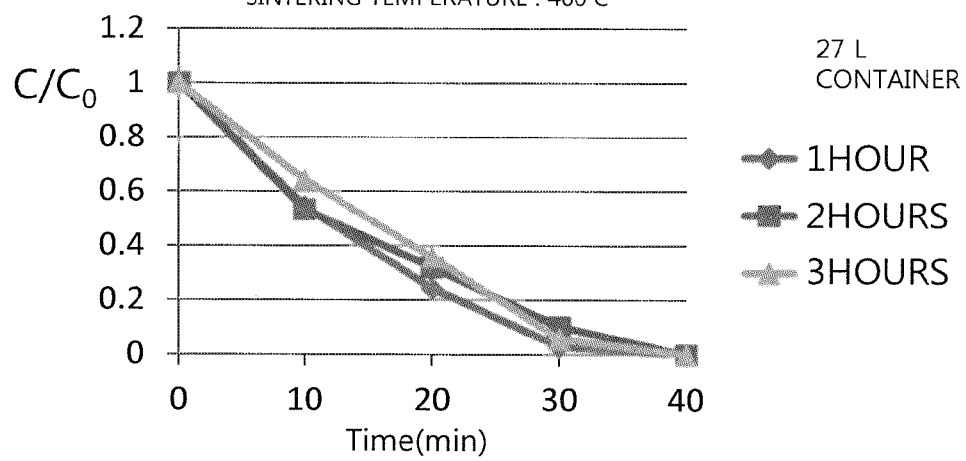

[Fig. 24]
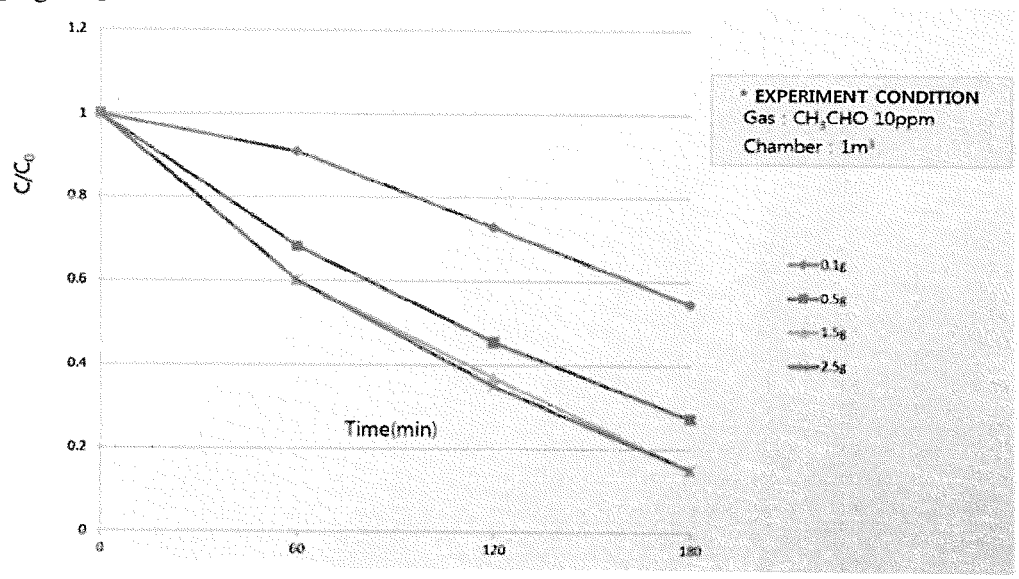

COMPACT AIR CLEANER USING UV LED AND PHOTOCATALYTIC FILTER

CROSS REFERENCE TO RELATED APPLICATIONS

This patent document is a 35 U.S.C. § 371 National Stage application of PCT Application No. PCT/KR2015/011867, filed on Nov. 5, 2015, which further claims the benefits and priority of prior Korean Patent Application Nos. 10-2014-0153955 filed on Nov. 6, 2014, 10-2001-0153956 filed on Nov. 6, 2014, 10-2014-0153957 filed on Nov. 6, 2014, 10-2014-0153958 filed on Nov. 6, 2014, 10-2014-0153959 filed on Nov. 6, 2014, 10-2014-0153960 filed on Nov. 6, 2014, and 10-2014-0173020 filed on Dec. 4, 2014. The entire disclosures of the above applications are incorporated by reference in their entirety as part of this document.

TECHNICAL FIELD

The present invention relates to an air cleaner, and more particularly, to an air cleaner capable of exhibiting excellent deodorization performance while having a small size enough to be fitted into a vehicle cup holder for its use, of performing dust collection and sterilization as well as deodorization, of easily replacing a filter, and of preventing odors generated by a photocatalytic filter from leaking to the outside of the air cleaner even when the air cleaner repeatedly operates and stops.

BACKGROUND ART

Titanium oxide ($TiO_2$) has a high adhesive force regardless of the type of substrate coated therewith, and exhibits photocatalytic activity when light (mainly, ultraviolet light) that may cause a photo-excited reaction is radiated thereto.

In particular, a photocatalytic reaction using titanium oxide has antibacterial and deodorization effects, and is often employed for air cleaning. For example, a method of eliminating odors in air in such a manner that a photocatalytic reaction occurs by irradiating a photocatalytic filter coated with titanium oxide (a $TiO_2$ ceramic form filter) with ultraviolet light while air passes through the photocatalytic filter has been widely used.

Titanium oxide is typically used in the form in which it is coated on a base, rather than being used per se. Therefore, the shape of a photocatalytic filter coated with titanium oxide is generally determined according to the shape of the base.

Deodorization using titanium oxide is mainly employed in medium-large air conditioners, whereas it is rarely employed in compact or home air cleaners.

In a large air conditioner having a large flow amount of air and a large flow area of air, deodorization may be performed without any problems as long as the air conditioner generates intense ultraviolet light and includes a large-sized photocatalytic filter.

However, in a compact air cleaner, the size of a photocatalytic filter is limited, the size of a device for generating ultraviolet light is limited, and the flow amount of air is small. Accordingly, it is necessary to develop an air cleaner having a deodorization effect above a certain level even when the compact air cleaner has a compact photocatalytic filter and generates weak ultraviolet light. In particular, electricity consumption as well as noise must be considered in a home air cleaner. However, since conventional techniques focus on medium-large air conditioners, there is hardly any technology suitable to adapt to new environments.

When ultraviolet light is intensively radiated with the intention of increasing the efficiency of a photocatalytic filter in a compact air cleaner, the material in a region, to which the ultraviolet light is intensively radiated, is rapidly transmuted or the large quantity of electricity is consumed in the state in which the efficiency of the photocatalytic filter is not ensured. In addition, the costs of the compact air cleaner will be increased in that more UV LEDs are installed and UV LEDs have a short service life.

In addition, it may be expected that the air cleaner has increased efficiency when it uses UV LEDs, each having a peak wavelength of about 270 nm known as a wavelength range in which titanium oxide is most well absorbed. However, since the irradiance of ultraviolet light radiated from the UV LED having a peak wavelength of 270 nm is actually considerably weak compared to power used in the air cleaner, deodorization efficiency may be poor even though the UV LEDs having a peak wavelength of 270 nm are used in the air cleaner.

The shape or dimension of a photocatalytic filter, and the relationship between the photocatalytic filter and an ultraviolet light source must be newly researched such that the photocatalytic filter has high efficiency even when having a small size. In particular, the shape or dimension of the photocatalytic filter is closely related with air resistance, and thus a fan applied to a compact air cleaner has limited standard or performance. Therefore, in order for the compact air cleaner to have own function, it is important to smoothly maintain the flow of air by reducing resistance to the flow of air.

Moreover, there is a need to find a method of manufacturing a photocatalytic filter such that the photocatalytic filter itself may have high photocatalytic activation efficiency. The technique that can obtain a higher deodorization effect only by a photocatalytic filter having a small volume is one of techniques required for compact air cleaners.

In addition, when a compact air cleaner is configured of UV LEDs and photocatalytic filters, the arrangement order of fans and filters is a major consideration. Conventional medium-large air conditioners first filter out dust through dust collection filters and then perform deodorization using photocatalytic filters. However, these filters are major components that cause the pressure of air to be lowered. Therefore, even when this structure is applied to compact air cleaners, the photocatalytic filters may not properly exhibit functions compared to the case that it applied to the medium-large air conditioners.

In addition, harmful bacteria floating in air must be eliminated in home. In this case, it is difficult to apply HEPA filters, known to filter out bacteria, to small air cleaners since the HEPA filters have strong air resistance. Furthermore, when air resistance is increased due to the installation of the HEPA filters, this may rather affect the deodorization reactions of photocatalytic filters. Accordingly, it is necessary to find alternative methods for efficiently eliminating bacteria without interrupting the air flow in air cleaners.

In particular, the vehicle interior is a space that requires the installation of an air cleaner having high deodorization efficiency since odors due to smoking are rarely removed from the vehicle interior. Since the vehicle interior is very small, there is a need for an air cleaner which has the significant ability to purify air without occupying a large space. In particular, since the vehicle rolls heavily, the air cleaner need to have a structure that is properly maintained at a fixed position and to be easily installed, under such environments. In particular, since most of vehicle air cleaners are options provided from vehicle manufacturers, there is a problem in that the air cleaners installed in a vehicle cannot be continuously used other vehicles. Therefore, the demand for portable air cleaners will increase in the technical field of vehicle air cleaners.

In addition, when an air cleaner is used for a vehicle, the air cleaner is used only during the operation of the vehicle, and thus a use pattern in which the air cleaner operates and stops is repeated. According to the experiment of such a use pattern for an air cleaner having a photocatalytic filter, it may be seen that, when the air cleaner stops for a long time and operates again, odors are discharged from the outlet port of the air cleaner in the initial stage of operation thereof, compared to the case in which the photocatalytic filter is not applied to the air cleaner. Considering that the vehicle air cleaner having a small size repeatedly operates and stops and the operation time of the vehicle is short, customers may feel displeasure with odors discharged from the air cleaner whenever the vehicle is operated, resulting in a deterioration in satisfaction for product use.

Moreover, if it is difficult to perform the maintenance of an air cleaner and manufacture it by the overemphasis of functions thereof, commercial values are deteriorated and a user experiences inconvenience. For this reason, there is a need for an air cleaner which has a simple structure, is easily manufactured, and is convenient for maintenance.

DISCLOSURE OF INVENTION

Technical Problem

Accordingly, the present invention has been made in view of the above-mentioned problem, and an object thereof is to provide an air cleaner capable of having high deodorization efficiency while having a small size using an UV LED and a photocatalytic filter, and to provide the ultraviolet irradiance of the UV LED, the peak wavelength thereof, the power source input thereto, the shape, size, dimension, material, and processing method of the photocatalytic filter, and the relationship between the UV LED and the photocatalytic filter.

It is another object of the present invention to provide an air cleaner capable of having high dust collection and sterilization efficiency as well as high deodorization efficiency.

It is another object of the present invention to provide an air cleaner capable of having a compact size enough to be fitted into a vehicle cup holder for its use, and of being easily fixed in a vehicle interior space.

It is another object of the present invention to provide an air cleaner capable of having low power consumption and noise while increasing the ability to purify air to a maximum level.

It is another object of the present invention to provide an air cleaner which is convenient for maintenance thereof.

It is another object of the present invention to provide an air cleaner which has a compact inner structure even though the air cleaner is complicated.

It is a further object of the present invention to find causes of odors generated in the initial stage of operation and thus prevent them in an air cleaner having a photocatalytic filter.

Solution to Problem

In accordance with an aspect of the present invention, there is provided an air cleaner which includes a photocatalytic UV LED (57) installed on an UV LED substrate (55), and a photocatalytic filter installed on a surface facing the photocatalytic UV LED while being spaced apart from the UV LED substrate. The air cleaner has the following technique features.

The photocatalytic filter may be configured such that TiO2 is coated on a base.

An irradiance of ultraviolet light measured on a front face of the photocatalytic filter may be 10 to 20 $mW/cm^2$, and preferably 14 to 15 $mW/cm^2$.

The ultraviolet light radiated from the photocatalytic UV LED may have a peak wavelength of 340 to 380 nm, and preferably a peak wavelength of 360 to 370 nm.

Power applied to the photocatalytic UV LED may have a voltage of 5 to 15 V and a current of 200 to 300 mA.

The photocatalytic filter may have a structure in which a plurality of cells (83) defining an air flow path in a direction toward the photocatalytic UV LED are arranged in parallel adjacent to each other. The photocatalytic filter may have a height (h) of 2 to 15 mm, and preferably a height (h) of 5 to 10 mm.

Each of the cells may have a square shape when viewed from a flow direction of air.

A frame as a partition wall for dividing the cells may have a thickness (t) of 0.3 to 1.2 mm, and preferably a thickness (t) of 0.5 to 0.7 mm.

Each of the cells may have an inner spacing distance of 1 to 4 mm, and preferably an inner spacing distance of 1.8 to 2.2 mm.

Each of the cells may have a density of 30 to 260 $cell/inch^2$, and preferably a density of 80 to 120 $cell/inch^2$.

The base may be a porous ceramic material.

The $TiO_2$ may be coated on the photocatalytic filter at a sintering temperature of 350 to 450° C. for a sintering time of 1 to 2 hours.

Air may flow from a portion, in which the UV LED substrate is installed, to a portion, in which the photocatalytic filter is installed.

An ultraviolet reflecting plate may be installed on a side between the UV LED substrate and the photocatalytic filter.

The external appearance of the front face of the photocatalytic filter may be a circular or square shape when viewed from the flow direction of air.

The photocatalytic filter may have an area of $4^2$ to $7^2$ $cm^2$ at a front face thereof, and a distance between the photocatalytic UV LED and the front face of the photocatalytic filter may be 2 to 3 cm. Preferably, the photocatalytic filter may have an area of $5.3^2$ to $5.7^2$ $cm^2$ at a front face thereof, and a distance between the photocatalytic UV LED and the front face of the photocatalytic filter may be 2 to 3 cm.

The UV LED substrate (55) may be equipped with a sterilizing UV LED (56) which radiates ultraviolet light having a sterilization wavelength in the same direction as an ultraviolet irradiation direction from the photocatalytic UV LED.

A second activated carbon filter (75) may be installed to a rear face of the photocatalytic filter.

The second activated carbon filter may include granular activated carbon.

The second activated carbon filter may be configured in a form of nonwoven fabric in which granular activated carbon is embedded.

The second activated carbon filter (75) may include pulp type activated carbon.

A dust collection filter (90) may be installed to a rear face of the photocatalytic filter.

The second activated carbon filter installed to the rear face of the photocatalytic filter may be closer to the photocatalytic filter than the dust collection filter installed to the rear face of the photocatalytic filter.

The second activated carbon filter installed to the rear face of the photocatalytic filter may be formed integrally with the dust collection filter installed to the rear face of the photocatalytic filter so as to form a filter member (93).

The UV LED substrate and the photocatalytic filter may be installed in an inner housing (30) in which air flows, the photocatalytic filter may be installed to come into contact with an inner wall of an inner housing having a relatively large cross-sectional area, and the UV LED substrate may be installed to be spaced apart from an inner wall of an inner housing having a relatively small cross-sectional area.

A lower housing (20) having a relatively small diameter may be disposed in a lower portion of the upper housing having a relatively large diameter, the inner housing (30) having a hollow inner space opened in vertical direction may be fixed while being spaced apart from an inner portion of the upper housing and an inner portion of the lower housing, a portion of the inner housing having a large cross-sectional area may be fixed corresponding to the upper housing, a portion of the inner housing having a small cross-sectional area may be fixed corresponding to the lower housing, and an inlet grate serving as a passage, through which air is introduced inward from the outside of the lower housing, may be formed at one side of an upper end of the lower housing.

Air inlet ports (302) formed at a lower end of the inner housing may be located at positions lower than the inlet grate, and the lower housing may be spaced apart from the inner housing at a height portion between the inlet grate and each air inlet port.

A fan (60) may be installed upstream of the portion, in which the UV LED substrate is installed, in the flow direction of air in the inner housing.

The fan for forcibly moving air from the outside of the inner housing to the inside thereof may be fixedly installed to a fan accommodation section (301) at the lower end of the inner housing, introduction sections (61) of the fan may be formed in left and right directions so as to face each other, the air inlet ports (302) may be formed in the left and right direction of the fan accommodation section (301) so as to face each other, the inlet grate may be formed in the front of the lower housing.

The inner housing may be divided into a left housing (31) and a right housing (32).

Each of the air inlet ports (302) may be provided with a first activated carbon filter.

The lower housing (20) may be divided into a front housing (21) and a rear housing (22). When the front housing (21) is separated, the installation section of the first activated carbon filter is exposed to the outside.

Each of the air inlet ports (302) may be formed with a pair of parallel stepped members (305), and the first activated carbon filter (70) may include a housing (71) having a width, which is press-fitted between the pair of the stepped members (305).

The housing (71) may be supported by a round portion of a screw fastening section (306) of the lower housing and the inner housing, so as to prevent the first activated carbon filter from being removed from the stepped members.

The housing (71) of the first activated carbon filter (70) may be formed with a pre-filter surface (72), and activated carbon may be received in the housing.

The housing (71) may have an elastic sealer (73) attached thereto, so as to prevent air from being introduced into a gap between the housing and the stepped members.

Air in the inner housing may be discharged rearward and upward through a discharge section (63) of the fan, and a streamlined extension duct (381) may be installed in the upper portion of the fan accommodation section (301) of the inner housing, the streamlined extension duct (381) having a cross-sectional area gradually enlarged as air flows upward in the streamlined extension duct from the discharge section (63).

A flow guide (37) for guiding diffusion of air flow to a duct having an enlarged diameter may be formed in the inner housing at the upper portion of the discharge section (63) of the fan.

The UV LED substrate may be installed at the upper portion of the streamlined extension duct (381) while being spaced apart therefrom, and the UV LED substrate may be installed to be inclined corresponding to the streamlined direction of the streamlined extension duct.

The photocatalytic filter (80) and the dust collection filter (90) may be installed in the inner housing so as to correspond to the height portion of the upper housing, and may be installed so as to be withdrawn in one direction from the inner housing.

The photocatalytic filter (80) may include a catalytic section (81), and an elastic bumper (82) surrounding the side of the catalytic section (81).

A portion of the side face may be cut such that a portion in front of both sides of the photocatalytic filter is exposed in a photocatalytic filter accommodation section (36) of the inner housing.

The dust collection filter (90) may be a second activated carbon filter-combined dust collection filter.

The dust collection filter (90) may include a filter member (93) for collecting dust, a frame (91) for fixing the filter member into the inner housing or withdrawing the filter member from the inner housing, and a handle (92) formed at the front face of the frame (91).

The second activated carbon filter-combined dust collection filter (90) may include a filter member (93) for adsorbing harmful gas and collecting dust, a frame (91) for receiving the filter member, and fixing the filter member into the inner housing or withdrawing the filter member from the inner housing, and a handle (92) formed at the front face of the frame (91).

An outlet section (34) may be formed downstream of the portion, in which the photocatalytic filter is installed, so that air is discharged through the outlet section from the inner housing.

The inner housing may have a streamlined reduction duct (382) formed at the upper portion thereof in order to guide the flow of air to the outlet section.

An ultraviolet emission prevention plate (39) may be installed upstream of the outlet section (34) in order to prevent ultraviolet light from being directly radiated to the outside through the outlet section.

The upper portion of the streamlined reduction duct may be provided with a PCB fixing section (33) for fixing a control PCB (51).

The control PCB (51) fixed to the upper portion of the inner housing and an upper face housing (40) covering the outlet section may be fixed in the upper portion of the PCB fixing section (33). The upper end of the upper housing may come into contact with the lower end of the outside edge of the upper face housing in the state in which the upper housing 10 is fixed in the upper portion of the inner housing (30).

The upper face housing (40) may be formed with an outlet grate (43) communicating with the outlet section (34).

The upper face housing (40) may be formed with buttons (41) for pressing the switch of the control PCB (51).

An internal power cable for supplying power from the control PCB (51) to the fan (60) and the UV LED substrate (55) and connecting them for control thereof may extend from the control PCB (51) to be close contact against the outer face of the inner housing (30), and then enter the inner space of the inner housing (30) through an internal power cable through-aperture (315) formed in the fan accommodation section (301).

The internal power cable extending to the inner space through the internal power cable through-aperture (315) may be connected to the fan (60), and may further extend along the inner space of the inner housing to be connected to the UV LED substrate (55).

The filters (80 and 90) may be installed to be withdrawn forward relative to the inner housing, and the internal power cable may extend in the state in which it is close contact against the left or right face of the inner housing.

The internal power cable through-aperture (315) may be formed in the upper portion in front of the fan accommodation section (301).

The control PCB (51) may be formed with an input power connector (512) configured such that the connector is exposed toward the right face to be fitted in the left direction or is exposed toward the left face to be fitted in the right direction.

The upper housing (10) may include a cylindrical side section (11), and a stepped section (12) which extends inward from the lower end of the side section. The lower housing (20) may include cylindrical side sections (211 and 221) having a smaller diameter than the upper housing, and stepped sections (213 and 223) formed at the upper portions of the side sections, thereby allowing the upper housing (10) to be fixed in the upper portion of the inner housing (30) in the state in which the upper housing (10) is inserted onto the lower housing (20) from the lower portion thereof.

The stepped section (12) may have a through-hole (13), and a cut section (215) may be formed in any one of the stepped sections (213 and 223). An external power cable connected to the input power connector (512) may extend to the outside through a space in which the through-hole (13) matches and communicates with the cut section (215).

The upper housing (10) may have a fastening protrusion section (14), which is formed at the inner face thereof and has a circumferentially inclined surface. The inner housing (30) may have a protrusion receiving groove (316), which is formed in the upper outer face thereof at a position corresponding to the fastening protrusion section (14), and a protrusion fixing groove (317), which faces protrusions for click feeling and is formed adjacent to the side of the protrusion receiving groove (316).

The protrusion receiving groove (316) may be opened at the bottom portion thereof, and the protrusion fixing groove (317) may be closed at the bottom portion thereof. The fastening protrusion section (14) on the inner face of the upper housing may be fitted into the protrusion receiving groove (316) from the lower portion thereof, and may move laterally and climb over the protrusions for click feeling so as to be fitted into the protrusion fixing groove (317), thereby allowing the upper housing to be fixed to the inner housing.

Any one of the stepped sections (213 and 223) formed at the upper portion of the lower housing may be formed with a recessed section (216) through which the fastening protrusion section (14) may pass when the upper housing is lifted or dropped in the state in which it is inserted onto the lower housing. The recessed section (216) may be formed immediately below the protrusion receiving groove (316).

The external power cable may have a terminal, which is formed at the end thereof and is bent in a "⌐" form.

Advantageous Effects of Invention

In accordance with the present invention, an air cleaner can have a compact size, low energy consumption, and high ability to purify air.

The air cleaner can have a high sterilization effect as well as high dust collection and deodorization effects.

The air cleaner can have a compact shape and size enough to be fitted into a cup holder for its use, and can be strong since it has a compact inner structure corresponding to such an external shape.

Since the air cleaner has a structure in which it is easily disassembled, a filter is attached and detached only by the minimal disassembly of the air cleaner, and the maintenance thereof is convenient, the maintenance of the filter can be convenient.

The air cleaner can prevent ultraviolet light from being emitted to external environments, and the present invention can remove harmful effect due to the ultraviolet light.

Since wiring is efficiently located in the compact and complicated inner structure of the air cleaner, the manufacturing, maintenance, and use thereof can be significantly convenient.

The present invention can easily replace an external power cable by the structure of a housing, and prevent the external power cable from being removed or damaged.

The air cleaner can increase purification efficiency by a photocatalytic reaction and simultaneously prevent odors generated by the photocatalytic filter from leaking to the outside of the air cleaner even when the air cleaner repeatedly operates and stops as in vehicles, thereby enhancing user's satisfaction.

Additional advantages, objects, and features of the invention will be set forth in part in the description which follows and in part will become apparent to those having ordinary skill in the art upon examination of the following or may be learned from practice of the invention.

BRIEF DESCRIPTION OF DRAWINGS

The above and other objects, features and other advantages of the present invention will be more clearly understood from the following detailed description taken in conjunction with the accompanying drawings, in which:

FIG. 1 is a perspective view illustrating an air cleaner according to an embodiment of the present invention;

FIG. 2 is an exploded perspective view illustrating the air cleaner of FIG. 1;

FIGS. 3 to 5 are respective perspective views illustrating the state in which the disassembled components of FIG. 2 are assembled;

FIG. 6 is a perspective view illustrating an upper housing when viewed from the top, according to the embodiment of the present invention;

FIGS. 7 to 10 are perspective views illustrating an inner housing, from which all outer housings (an upper housing, a lower housing, and an upper face housing) are decoupled and a first activated carbon filter is separated, when viewed from different directions;

FIG. 11 is a perspective view illustrating the air cleaner from which only the upper housing and front housing are decoupled, according to the embodiment of the present invention;

FIG. 12 is a perspective view illustrating the air cleaner from which the upper face housing, the upper housing, a rear housing, and a right housing are removed, according to the embodiment of the present invention;

FIG. 13 is a perspective view illustrating the air cleaner from which the upper face housing, the upper housing, the lower housing, and the right housing are removed, when viewed from the side, according to the embodiment of the present invention;

FIG. 14 is a perspective view illustrating the arrangement between a photocatalytic filter and an UV LED substrate;

FIG. 15 is a top view illustrating the photocatalytic filter;

FIG. 16 is a graph illustrating a decomposition rate of acetaldehyde according to the irradiance of ultraviolet light reaching the front face of the photocatalytic filter;

FIG. 17 is a graph illustrating the ultraviolet absorbance of the photocatalytic filter according to ultraviolet wavelengths;

FIG. 18 is a graph illustrating a removal rate of acetaldehyde according to ultraviolet wavelengths;

FIG. 19 is a graph illustrating a difference in deodorization rate of acetaldehyde according to the height (h) of the photocatalytic filter;

FIG. 20 is a graph illustrating a difference in deodorization rate of acetic acid according to the height (h) of the photocatalytic filter;

FIG. 21 is a graph illustrating deodorization performance for each sintering temperature of the photocatalytic filter when 2 g of $TiO_2$ is sintered for one hour;

FIG. 22 is a graph illustrating deodorization performance for each sintering temperature of the photocatalytic filter when 2.5 g of $TiO_2$ is sintered for one hour;

FIG. 23 is a graph illustrating deodorization performance for each sintering temperature of photocatalytic filters manufactured by sintering 2.5 g of $TiO_2$ at a sintering temperature of 400° C. for different times; and FIG. 24 is a graph illustrating photocatalytic reaction efficiency according to the amount of photocatalytic material loaded into the photocatalytic filter.

MODE FOR THE INVENTION

The present invention may be embodied in different forms and should not be construed as limited to the embodiments set forth herein. Rather, these embodiments are provided so that this disclosure will be thorough and complete, and will fully convey the scope of the present invention to those skilled in the art.

Particular features, structures, or characteristics described in connection with the embodiment are included in at least one embodiment of the present disclosure and not necessarily in all embodiments. Furthermore, the particular features, structures, or characteristics of any specific embodiment of the present disclosure may be combined in any suitable manner with one or more other embodiments or may be changed by those skilled in the art to which the embodiments pertain.

Reference will now be made in detail to embodiments of the present invention, examples of which are illustrated in the accompanying drawings.

[External Appearance of Air Cleaner]

Referring to FIG. 1 that is a perspective view of an air cleaner according to an embodiment of the present invention, the air cleaner includes an upper housing 10 having a relatively large diameter, a lower housing 20 having a slightly smaller diameter than the upper housing, and an upper face housing 40 located at the upper end of the upper housing.

The central portion of the upper face housing 40 is provided with two respective buttons 41 for turning on/off the air cleaner and adjusting the flow rate of air (wind strength) in the air cleaner, and is also provided with two respective lamps for identifying the on/off state of the air cleaner and the flow rate of air (wind strength) therein. The air cleaner may be operated, for example, by pressing the on/off button for several seconds in order to turn on/off the air cleaner, and by pressing the wind strength adjustment button once in order to adjust the wind strength.

As illustrated in the drawing, since an outlet grate 43 for the discharge of purified air is installed at one side of the upper face housing 40, the purified air is discharged through the outlet grate, and large foreign substances are prevented from being introduced into the air cleaner from the outside by the shape of the outlet grate.

The upper housing 10 has a larger diameter than the lower housing 20. The upper housing has a larger diameter than the upper end portion of a vehicle cup holder, thereby enabling the upper housing of the air cleaner to be prevented from being inserted into the cup holder when the air cleaner is fixedly fitted into the vehicle cup holder.

The lower housing 20 is configured of two divided bodies, i.e. a front housing 21 and a rear housing 22. An inlet grate 212 is formed in the vicinity of the upper end of the front housing 21.

Accordingly, outside air is introduced into the lower housing 20 through the inlet grate 212, is purified by the inner structure of the air cleaner, and is then discharged through the outlet grate 43 of the upper face housing 40.

[Configuration and Fastening Structure of Air Cleaner]

FIG. 2 is an exploded perspective view illustrating the air cleaner of FIG. 1. FIGS. 3 to 5 are respective perspective views illustrating the state in which the disassembled components of FIG. 2 are assembled. The reason the upper housing 10 is arranged at the lowest side in FIGS. 2 to 5 is because the upper housing is fastened upward from the lower end of the air cleaner.

As illustrated in FIG. 1, the upper housing 10, the lower housing 20, and the upper face housing 40 define the external appearance of the air cleaner. As illustrated in FIG. 2, an inner housing 30 is installed in the air cleaner. The inner housing is coupled to the upper housing 10, the lower housing 20, and the upper face housing 40, which are outer housings, and serves to securely fix the outer housings.

As illustrated in the drawing, the inner housing 30 is configured of two divided bodies, i.e. a left housing 31 and a right housing 32. The direction in which the inner housing 30 is divided into the left and right housings 31 and 32 is perpendicular to the direction in which the lower housing 20 is divided into the front and rear housings 21 and 22. The housings may be more securely fastened to each other in terms of structure by allowing the lower housing 20 as one of the outer housings and the inner housing 30 to be configured in the different divided directions.

A PCB fixing section 33 is arranged on the upper portion of the inner housing 30, such that a control PCB 51 does not cover an outlet section 34 located at one side of the upper end of the inner housing. In addition, the space in the PCB fixing section 33 is defined by a streamlined reduction duct 382 formed in the lower portion of the PCB fixing section. As will be described later, the streamlined reduction duct 382 is formed at the upper end of the inner housing 30 in order to guide air flowing in the inner housing toward the outlet section 34. The PCB fixing section 33 is provided in the space defined by the streamlined reduction duct 382, thereby enabling the inner space of the compact air cleaner to be effectively utilized.

An external power cable through-hole 322, which serves as a path for connection of an external power cable to the control PCB 51, is formed in the right of the portion of the inner housing, which is provided with the PCB fixing section 33. The left of the above portion is formed with an internal power cable through-hole 312 serving as a connection path of an internal power cable for supplying power from the control PCB 51 to a fan 60 and an UV LED substrate 55, which will be described later.

Within the air flow duct structure formed by the inner housing 30, a dust collection filter 90 and a photocatalytic filter 80 are first installed from top to bottom, as illustrated in the drawing, so as to be adjacent to each other, and the UV LED substrate 55 is fixed in the lower portion of the air flow duct structure in the state in which the UV LED substrate is spaced apart from the photocatalytic filter by a predetermined distance. UV LEDs on the UV LED substrate are arranged toward the photocatalytic filter.

The dust collection filter 90 and the photocatalytic filter 80 perfectly shield the air flow duct structure, so that air flowing in the duct necessarily passes through the photocatalytic filter 80 and the dust collection filter 90. On the other hand, the UV LED substrate 55 is installed by a substrate fixing section 303 protruding inward from the inner wall of the inner housing 30 so as to be spaced apart from the inner wall of the inner housing 30, thereby enabling air to flow in the space therebetween. As will be described later, One UV LED having a peak wavelength of 275 nm for sterilization is installed on the central portion of the UV LED substrate 55, and three UV LEDs having a peak wavelength of 365 nm for activation of the photocatalytic filter are installed around the central portion thereof.

Here, it is noted that the dust collection filter 90 and the photocatalytic filter 80 are withdrawn forward so as to be replaceable. Due to the arrangement structure in which the withdrawal directions of the filters do not overlap with the above-mentioned arrangement directions of the external power cable (right) and the internal power cable (left), it is not necessary to separate the cables when the filters are replaced.

The dust collection filter 90 may be a second activated carbon filter-combined dust collection filter which is formed integrally with a second activated carbon filter 75.

The lower end portion of the inner housing 30 is provided with a fan accommodation section 301 for accommodating and fixing the fan 60, and air inlet ports 302, through which air sucked by the fan is introduced, are respectively formed in the left and right faces of the fan accommodation section 301.

The fan 60 used for the air cleaner of the present invention has a structure in which air may efficiently flow even in a small space. As illustrated in the drawing, the central portion of the fan 60 is formed with an introduction section 61 opened at both sides thereof, and air introduced through the introduction section 61 is forcibly discharged to a discharge section 63 formed at the rear upper portion of the fan by the rotation of blades.

A flow guide 37, which has a shape for widely distributing the flow of air discharged from the discharge section having a small cross-section, is installed in the upper portion of the discharge section 63 in the inner housing 30. In addition, a streamlined extension duct 381 is formed in the lower portion of the inner housing in order to widely distribute the flow of air discharged from the discharge section. By such a flow guide 37 and streamlined extension duct 381, the flow of air may be smoothly guided while kinetic energy of air discharged at high speed from the small outlet is minimally lost.

The periphery of each air inlet port 302 formed in the lower end of the inner housing 30 is formed in a flat plate shape, and stepped members 305 are longitudinally formed at the upper and lower ends of the air inlet port 302, respectively. The stepped members 305 are fastened to a first activated carbon filter 70 covering the associated air inlet port 302.

The air inlet port 302 formed in the lower end of the inner housing 30 is covered by the first activated carbon filter 70, as illustrated in the drawing. The first activated carbon filter 70 includes a housing 71 for maintaining the shape thereof, and pre-filter surfaces 72 which are formed on the opening portion of both sides (a surface facing the air inlet port 302 and a surface opposite thereto) of the housing 71.

Each of the pre-filter surfaces 72 has a function for preventing activated carbon accommodated in the inner space of the housing from flowing out of the housing, together with a pre-filter function for filtering out dust.

The activated carbon in the first activated carbon filter 70 adsorbs odor particles in air for deodorization. When activated carbon is frequently used, the adsorptive power of activated carbon is lowered and it is difficult to regenerate it. Thus, the present invention configures a detachable structure in consideration of the replacement of the first activated carbon filter 70.

As described above, the periphery of the air inlet port 302 has a flat plate shape, and the stepped members 305 are respectively formed at the upper and lower ends of the air inlet port. In addition, the first activated carbon filter 70 has a width (when the first activated carbon filter has a square shape, a length of one side of the square) which is equal to or slightly greater than the distance between the two stepped members. Accordingly, the first activated carbon filters may be respectively installed to the left and right sides of the lower end of the inner housing by press-fitting the upper and lower ends of each first activated carbon filter between the associated stepped members without separate additional fastening members.

As illustrated in the drawing, an elastic sealer 73 is installed around the housing 71 of the first activated carbon filter in order to prevent air from being introduced into the gap between the housing 71 of the first activated carbon filter and the flat plate around the air inlet port 302.

In addition, the housing of the first activated carbon filter has a trapezoid cross-sectional shape in which the surface of the housing coming into contact with the inner housing is the largest surface and the opposite surface thereof is gradually narrowed, as illustrated in the drawing. The inclined surface of the edge of the first activated carbon filter formed by such a structure engages with the round portion of a screw fastening section 306 for fastening the inner housing 30 to the rear housing 22, as illustrated in FIG. 4. Due to such a structure, the first activated carbon filter is supported toward the coupling surface of the inner housing while engaging with the screw fastening section.

The fastening structure of the housings will be described. First, the two divided bodies of the inner housing 30 are fastened by screws or the like in the state in which the fan 60 and the UV LED substrate 55 are fixed to any one side of the inner housing 30. In the embodiment of the present invention, the internal power cable for connecting the control PCB 51, the fan 60, and the UV LED substrate 55 is disposed in the left housing 31 while passing through the internal power cable through-hole 312. Therefore, it is preferable that, after the fan 60 and the UV LED substrate 55 are fixed to the left housing 31 having the internal power cable through-hole 312, the right housing 32 be covered so that the left and right housings are fastened.

Next, as illustrated in FIG. 4, the control PCB 51 is fixed to the substrate fixing section 303, provided at the upper end of the inner housing, by screws or the like, and the dust collection filter 90 and the photocatalytic filter 80 are respectively fitted into a dust collection filter accommodation section 35 and a photocatalytic filter accommodation section 36.

Next, as illustrated in FIG. 5, after the rear housing 22 is fixed to the lower portion of the inner housing by screws (see the screw fastening groove in the rear housing and the screw fastening section 306 in the inner housing), the front housing 21 is fastened to the front of the rear housing such that the lower housing 20 is fixed to the inner housing 30, and the upper face housing 40 is fixed to the upper end of the inner housing 30.

Finally, the upper housing 10 is lifted from bottom in the state illustrated in FIG. 5, so as to be fitted to the other housings, and is then fastened as illustrated in FIG. 1. Consequently, the assembly of the housings is completed.

[Relationship Between Housing Structure and Filter Replacement Structure in Air Cleaner]

In the present invention, the front and upper housings 21 and 10 may be sequentially and securely coupled without fastening using screws in an alternative manner, unlike when the other housings are fastened. In accordance with the present invention, the upper housing 10 may be decoupled without separate tools in the state illustrated in FIG. 5, and the front housing 21 may be decoupled without separate tools after the separation of the upper housing.

Hereinafter, the fastening structure of the front and upper housings will be described.

FIG. 6 is a perspective view illustrating the upper housing when viewed from the top, according to the embodiment of the present invention.

The upper housing 10 includes a cylindrical side section 11, and a stepped section 12 which extends inward from the lower end of the side section. The inner diameter of the upper housing defined by the stepped section 12 is equal to or slightly greater than the diameter of the lower housing 20. Therefore, the upper housing 10 may be inserted onto the lower housing 20 from the lower end portion thereof to be lifted to the upper portion of the inner housing 30, in the state in which the lower housing 20 is coupled to the inner housing 30.

The lower housing 20 includes cylindrical side sections 211 and 221 having a smaller diameter than the upper housing, stepped sections 213 and 223 formed outwardly at the upper portions of the side sections, and stepped side sections 214 and 224 extending upward from the end portions of the stepped sections. When the upper housing 10 is inserted onto the lower housing 20 and is fitted to the upper portion thereof, the stepped sections 213 and 223 of the lower housing 20 come into contact with the stepped section 12 of the upper housing 10, thereby restricting the upper housing from moving upward. Consequently, the upper end of the upper housing comes into contact with the upper face housing 40 at the restricted height of the upper housing.

As illustrated in FIG. 6, the upper housing has a fastening protrusion section 14 and alignment protrusion sections 15, which are formed in the inner surface thereof. The front stepped section 213 and front stepped side section 214 of the front housing 22 have a recessed section 216 formed at a position corresponding to the fastening protrusion section 14. The rear stepped section 223 of the rear housing 22 has alignment grooves 226 formed at positions corresponding to the alignment protrusion sections 15.

Accordingly, when the upper housing 10 is inserted onto the lower housing 20 and lifted, the upper housing 10 may be fully lifted to the fastening position in the state in which the fastening protrusion section 14 and the alignment protrusion sections 15 are respectively aligned with the recessed section 216 and the alignment grooves 226.

Meanwhile, as illustrated in FIG. 8, the inner housing 30 has a protrusion receiving groove 316 and a protrusion fixing groove 317, which are formed in the side face thereof and are adjacent to each other. Both of the protrusion receiving groove 316 and the protrusion fixing groove 317 have a shape corresponding to the fastening protrusion section 14. However, the protrusion receiving groove 316 is opened at the bottom portion thereof, and the protrusion fixing groove 317 is closed at the bottom portion thereof. Protrusions for click feeling are formed between the protrusion receiving groove and the protrusion fixing groove.

As described above, when the fastening protrusion section 14 and the alignment protrusion sections 15 are respectively aligned with the recessed section 216 and the alignment grooves 226, and the upper housing 10 is fully lifted to the fastening position, the fastening protrusion section 14 formed in the inner surface of the upper housing 10 is received in the protrusion receiving groove 316. In this state, when the inclined surface (see FIG. 6) of the fastening protrusion section 14 climbs over the protrusions for click feeling between the protrusion receiving groove and the protrusion fixing groove by rotating the upper housing 10, the fastening protrusion section 14 is fixed into the protrusion fixing groove 317, thereby perfectly fixing the upper housing 10.

That is, in this state, the upward movement of the upper housing 10 is restricted by the upper face housing 40 and the stepped sections 213 and 223. The rotation of the upper housing is restricted by the protrusion and wall formed at the left and right sides of the protrusion fixing groove 317. In addition, the downward movement of the upper housing is restricted by the bottom portion of the protrusion fixing groove 317 closed by the fastening protrusion section 14.

As such, when the upper housing 10 is fixed, the front housing 21 is also restricted by the upper and rear housings 10 and 22. In particular, since the upper housing 10 is fixed in the form of surrounding the lower housing 20, the front housing 21 may also be securely fixed without separate additional screw fastening. However, since the upper housing 10 surrounds only the upper portion of the lower housing 20, the front housing 21 may be maintained in a securely fixed state as long as the bottom surface of the front housing 21 is fastened to the bottom surface 229 of the rear housing in a snapping manner.

Meanwhile, the upper housing 10 has a through-hole 13, which is formed at a position corresponding to a cut section 215 of the front housing 21. The through-hole 13 has a size for allowing the pass of the external power cable. The cut section 215 is further cut by an angle allowing the fastening protrusion section 14 of the upper housing to rotate between the protrusion receiving groove and the protrusion fixing groove, while the external power cable passes through the cut section.

As illustrated in FIG. 5, the cut section 215 is located near at the right housing 32 in the state in which the lower housing 20 is fastened to the inner housing 30. This is to secure the movement path of the external power cable. The external power cable is connected to an input power connector 512 of the control PCB 51 through the external power cable through-hole 322 in the right housing 32, and then may extend to the outside by passing through the through-hole 13 and the cut section 215 through the space between the right housing 32 and the upper housing 10.

The input power connector 512 may consist of sockets to which the terminal (not shown) of the external power cable may be fitted. This terminal/socket structure enables the external power cable to be easily replaced. For example, since a cigar jack having 12V DC power is used when the air cleaner of the present invention is used for a vehicle, whereas 220V AC power is used when the air cleaner is used for home or offices, there is a possibility that the external power cable is replaced. Thus, the external power cable having the terminal/socket structure suitable for using environment is preferably connected to the control PCB 51.

Here, it is noted that the fitting direction of the terminal is fitted is perpendicular to the withdrawal direction of the external power cable. That is, the terminal of the external power cable is fitted in a diameter direction, and the external power cable is withdrawn in a downward direction. Therefore, when the terminal of the external power cable has, for example a "⌐" shape, the terminal is supported in the connection direction thereof by the inner surface of the upper housing 10, thereby preventing the external power cable from being removed even though the external power cable is pulled from the outside.

This fastening structure between the upper housing and the front housing enables the dust collection filter 90 of the air cleaner to be replaced by decoupling only the upper housing without separate tools, when the replacement of the dust collection filter is required. That is, in the order reverse to the above fastening process, the fastening protrusion section 14 is removed from the protrusion fixing groove 317 by climbing over the protrusions for click feeling by the reverse rotation of the upper housing, and is returned to the protrusion receiving groove 316. The upper housing is then decoupled downward. This state is a state illustrated in FIG. 5. In this case, the insertion section of the dust collection filter 90 is exposed as illustrated in the drawing. Thus, the dust collection filter 90 can be easily replaced by simply decoupling the upper housing.

As illustrated in FIG. 10, when a handle 92 of the dust collection filter 90 is pulled, the dust collection filter may be withdrawn. In this state, a filter member 93 in a frame 91 is replaced.

As described above, after the separation of the upper housing, the front housing 21 may be decoupled from the rear housing without separate tools. Therefore, as illustrated in FIG. 11, the photocatalytic filter 80 and the first activated carbon filter 70 can also be replaced through the portion of the inner housing 30 which is exposed due to the separation of the front housing 21.

FIGS. 7 to 10 are perspective views illustrating the inner housing, from which all outer housings (the upper housing, the lower housing, and the upper face housing) are decoupled and the first activated carbon filter is separated, when viewed from different directions. FIG. 11 is a perspective view illustrating the air cleaner from which only the upper housing and front housing are decoupled, according to the embodiment of the present invention.

The inner housing of the air cleaner according to the embodiment of the present invention will be described. All of the dust collection filter 90, the photocatalytic filter 80, and the first activated carbon filter 70 may be inserted into or removed from the inner housing. Accordingly, after the separation of the upper housing 10, the dust collection filter 90 may be replaced by pulling the handle 92 of the dust collection filter exposed to the front face of the inner housing. After the separation of the front housing 21, the photocatalytic filter exposed to the front face of the inner housing may be withdrawn.

As illustrated in FIGS. 14 and 15, since a catalytic section 81 of the photocatalytic filter is manufactured by sintering $TiO_2$ to a ceramic base in the form of lattice, it has high hardness and brittleness. Accordingly, as illustrated in the drawings, the periphery of the catalytic section 81 is surrounded by an elastic bumper 82, so that the catalytic section is protected from impact and is pressed against the inner housing 30.

The efficiency of the $TiO_2$ coated photocatalytic filter is reduced over time since foreign substances adhere to the surface of the photocatalytic filter, but it is difficult to replace the photocatalytic filter due to a high price. For this reason, the techniques related to the regeneration of filters have been consistently developed. Thus, there is a need for a detachable structure in order to replace or regenerate the photocatalytic filter. However, since the photocatalytic filter has the structure in which the periphery of the catalytic section 81 is surrounded by the elastic bumper 82, as described above, it is difficult to form a handle for detachably attaching the photocatalytic filter to the inner housing 30 as in the dust collection filter. In this regard, as illustrated in FIGS. 7 to 11, instead of the structure in which only the front face portion of the inner housing 30 is opened, the front face and a portion of the side face of the photocatalytic filter 80 fitted into the inner housing 30 are exposed together by partially cutting the side face communicating with the front face portion of the inner housing. Through such a structure of the inner housing, both sides of the photocatalytic filter may be gripped by user's hands, thereby enabling the photocatalytic filter to be easily withdrawn.

[Electric Connection Structure of Air Cleaner]

Referring FIG. 8, the surface of the left housing 31 of the air cleaner according to the present invention is formed with the internal power cable through-hole 312, an internal power cable through-groove 313, and an internal power cable guide groove 314. An internal power cable through-aperture 315 is formed in the front upper portion of the fan accommodation section 301.

Accordingly, the internal power cable connected to the control PCB 51 for supplying power to the fan 60 and the UV LED substrate 55 enters the inner space of the inner housing by sequentially passing through the internal power cable through-aperture 315 via the internal power cable through-hole 312, the internal power cable through-groove 313, and the internal power cable guide groove 314 along the outer surface of the inner housing from the control PCB 51 fixed to the PCB fixing section 33. The internal power cable entering the inner space is connected to the fan 60 installed at the lower end of the inner housing, and further extends to be connected to the UV LED substrate 55. The air cleaner of the present invention can further increase the flow acceleration of air by the fan by maintaining the airtightness of the inner housing since the internal power cable enters the inner space of the inner housing through the internal power cable through-aperture 315, formed in the fan accommodation section 301, which is a gateway to the inner space from the outer space (if the internal power cable is inserted into the inner housing through another portion perforated in the inner housing, a portion of air flowing in the inner housing may be leaked through the gap between the perforated portion and the internal power cable).

It may be seen that the internal power cable is easily inserted into the inner housing through the outlet section 34 of the inner housing 30 adjacent to the control PCB 51. However, since the air flow path in the inner housing is blocked by the dust collection filter 90 and the photocatalytic filter 80, it is impossible to insert the internal power cable along this path (if the cable is arranged along the path, the inside air is bypassed around the cable, with the consequence that the air cleaning efficiency by the filters may be deteriorated). As described above, the filters must be replaced through the front the inner housing. Thus, in the present invention, the internal power cable is connected through one side face of the inner housing in the above-mentioned manner.

As illustrated in FIG. 10, the internal power cable through-hole 312 and the external power cable through-hole 322 are formed in both sides of the inner housing so as not to interfere with the withdrawal direction of the filter. In the air cleaner of the present invention having a structure in which it is very small and the filters are detachably attached through the front face of the inner housing, the inner space of the air cleaner can be effectively utilized by the structure in which the internal and external power cables are respectively connected along the paths on the left and right faces of the inner housing. Consequently, the air cleaner can a more compact configuration.

[Flow Path in Air Cleaner]

FIG. 12 is a perspective view illustrating the air cleaner from which the upper face housing, the upper housing, the rear housing, and the right housing are removed, according to the embodiment of the present invention. FIG. 13 is a perspective view illustrating the air cleaner from which the upper face housing, the upper housing, the lower housing, and the right housing are removed, when viewed from the side, according to the embodiment of the present invention.

The flow path in the air cleaner according to the embodiment of the present invention will be described. Air introduced through the inlet grate 212 of the front housing by negative pressure generated by the fan is introduced into the introduction section 61 of the fan 60 through the first activated carbon filter 70 and the air inlet port 302 at both sides of the lower end of the inner housing 30 via the space between the lower housing and the inner housing. Next, air discharged upward from the discharge section 63 by the fan is uniformly distributed to the duct structure having an enlarged diameter by the flow guide 37 and the streamlined extension duct 381, and moves upward.

The flow guide 37 is inclined forward in a streamlined form as moving upward. The UV LED substrate 55 is also installed inclined slightly upward as it is directed forward such that the direction of light radiated from the UV LEDs on the substrate is without significantly departing from the photocatalytic filter. As seen in FIGS. 13 and 2, the substrate is arranged such that the whole periphery thereof is spaced apart from the air flow duct formed by the inner housing, thereby allowing the flow of air to be smoothly guided in order to prevent the flow energy of air to be lost.

Referring to FIGS. 12 and 13, the streamlined extension duct 381 has a diameter which is gradually enlarged forward as moving upward in the flow of air. In other words, the flow path of air introduced into the lower housing 20 through the inlet grate 212 from the outside is also enlarged by the streamlined extension duct 381 while the air moves downward toward the air inlet port 302 at the lower end of the inner housing 30. That is, the streamlined extension duct 381 functions to enlarge the cross-sectional area of the air flow path in the inner housing, and to enlarge the cross-sectional area of the air flow path in the space between the lower housing 20 and the inner housing 30. Through these air flow structure and duct structure of the present invention, the loss of air flow can be minimized and the air cleaner can have a compact structure.

Next, the air moved upward by the fan is guided by the above-mentioned configuration to pass through a plurality of through-holes formed in the photocatalytic filter 80, and then passes through the dust collection filter 90.

Here, it is noted that the UV LED substrate 55 is disposed at the lower portion of the inner housing corresponding to the height of the lower housing 20 having a relatively small diameter, and the photocatalytic filter 80 and the dust collection filter 90 are disposed at the upper portion of the inner housing corresponding to the height of the upper housing 10. That is, the inner housing has an enlarged diameter at the height of the stepped section between the lower housing and the upper housing. The UV LED substrate 55, which must be spaced apart from the photocatalytic filter by a predetermined distance despite having a relatively small size, is disposed in the small diameter section of the inner housing. The photocatalytic filter, which must be manufactured to have a slightly large size in order to maximally secure the contact area with air, is disposed in the large diameter section of the inner housing. The dust collection filter, in which the pressure drop of air is largely generated, is disposed in the large diameter section of the inner housing in order to increase the cross-sectional area of the filter through which air passes. Through such structures, the present invention can increase air purification efficiency while manufacturing compact products.

The air passing through the filters 80 and 90 is again guided to the outlet section 34 narrowed by the streamlined reduction duct 382, and is discharged to the outside.

The streamlined reduction duct 382 has a streamlined shape so as to reduce the cross-sectional area of air flow and reduce the loss of air flow, and thus the upper space of the streamlined reduction duct may be utilized as the PCB fixing section 33. The control PCB is fixed to the PCB fixing section 33 so that the air cleaner may be operated and the operation state of the air cleaner is identified from the upper face thereof. The structure of the present invention in which, considering that the air cleaner is fitted into the cup holder for its use, the buttons of the air cleaner are disposed on the upper face thereof and the discharge direction of air is directed upward from the upper face thereof, may well match with the use state of the present invention. The streamlined reduction duct structure allows the loss of air flow to be reduced and the formation space of the control PCB 51 to be secured while air is guided to the narrow outlet section. Consequently, the air cleaner can have a more compact configuration.

Meanwhile, an ultraviolet emission prevention plate 39 is formed in the lower portion of the outlet section 34 in order to prevent ultraviolet light from the UV LED substrate from being directly radiated to the outside through the outlet section. Thereby, it is possible to previously prevent a user from having doubt about the harmfulness of ultraviolet light.

In the air cleaner of the present invention, the introduction position and direction of air are directed forward from the upper end of the lower housing 20 (from the bottom portions of the stepped sections in the upper and lower housings), and the discharge position and direction of air are directed upward from the upper face of the upper face housing 40. This arrangement of inlet and outlet in different directions prevents the purified and discharged air from being introduced again into the inlet port.

In addition, air purification efficiency can be further increased by disposing the air inlet port in the lower housing, considering that acetaldehyde and acetic acid decomposed by the photocatalytic filter sink because they are heavier than air.

In addition, since the present invention considers that the air cleaner is fitted into the cup holder for its use, the inlet grate 212 is formed at the upper end of the lower housing such that air is introduced therethrough. The streamlined extension duct 381 is formed in the narrow space between the lower housing 20 and the inner housing 30 in order to minimize the loss of air flow, and the air inlet ports 302 as passages for entering the inner housing are formed at both sides of the lower portion of the inner housing in a direction perpendicular to the enlarged direction of the streamlined extension duct. In addition, the present invention secures the cross-sectional area of air flow by the streamlined extension duct in the inner housing. Thus, the optimal flow path of air can be realized so as to be suitable for the size and use of air cleaner.

[Filter Arrangement in Air Cleaner]

In accordance with the arrangement order of the filters according to the air flow path in the air cleaner of the present invention, air first passes through the first activated carbon filter 70 consisting of a pre-filter and activated carbon so that large particles of dust in the air is filtered by the pre-filter, harmful gases such as ammonia ($NH_4$) and acetic acid ($CH_3COOH$) are adsorbed and removed by the activated carbon, and acetaldehyde ($CH_3CHO$) is decomposed by the photocatalytic reaction of the photocatalytic filter 80. Then, after harmful gas causing odors is adsorbed and fine dust is filtered through the second activated carbon filter-combined dust collection filter 90 consisting of nonwoven fabric having activated carbon therein and a fiber filter, the air is discharged.

The pre-filter previously filters out large particles of dust, and prevents the efficiency of the photocatalytic filter from being lowered due to adhesion of foreign substance such as dust to the surface of the photocatalytic filter located in the rear. In the present invention, in order to increase the decomposition efficiency of acetaldehyde which is later reacted compared to ammonia and acetic acid in the competitive reaction of photocatalyst, after ammonia and acetic acid, which are superior than acetaldehyde in the competitive reaction, are first adsorbed (acetaldehyde being rarely adsorbed by activated carbon), the photocatalytic reaction occurs in the state in which the concentration of other gas which is superior than acetaldehyde in the competitive reaction is diluted. Thereby, the acetaldehyde may be initially decomposed through the photocatalytic reaction in early stage.

One of the major features of the present invention is to install the activated carbon filters in both front and rear of the photocatalytic filter. The reason the activated carbon filter is disposed in front of the photocatalytic filter is as described above. Meanwhile, the reason the activated carbon filter is disposed behind the photocatalytic filter is because odors are generated in the initial stage of operation of the photocatalytic filter as shortly mentioned above.

When the air cleaner including the photocatalytic filter and the light source is operated again in the state in which it is not operated for several hours, odors are generated from air blown from the air cleaner. According to various experiment for identifying causes of such odors, it is identified that the odors in the initial stage of operation of the air cleaner having the photocatalytic filter is not odors generated from the base of the photocatalytic filter, it is not determined whether or not odors are generated according to the type of base, and the present status or type of additive (dispersant) used during photocatalytic coating is not the causes of odors.

In addition, it is identified that the less the amount of photocatalytic material ($TiO_2$) loaded into the base, the less the generation of odors in the initial stage of operation.

In addition, it is identified that the longer the time for which ultraviolet light is not radiated to the photocatalytic filter, the more the odors are generated when the air cleaner is operated again. In addition, it is identified that, even when odors are initially generated when the air cleaner is operated again, the odors are eliminated over time.

From these facts, it may be guessed that when the photocatalytic filter is not operated for a long time in the state in which the light source providing energy for activating photocatalyst is turned off, gas causing odors is adsorbed onto and accumulated in the photocatalytic material coated on the photocatalytic filter. And it may be guessed that, thus, when the air cleaner is turned on in this state, gas causing odors adsorbed onto the photocatalytic material is separated therefrom and flows with the air flowing by the fan.

According to the result of experiment, it is identified that, when activated carbon is disposed behind the photocatalyti filter, the activated carbon may remove odors generated in the initial stage of operation of the air cleaner by adsorbing gas which is adsorbed onto and then separated from the photocatalytic material. That is, it may be identified that the gas causing odors, which is adsorbed onto and then separated from the photocatalytic material, is well adsorbed by activated carbon.

Accordingly, in the present invention, the activated carbon filters are disposed in both front and rear of the photocatalytic filter, instead of simply disposing one activated carbon filter in the path for air cleaning. Therefore, although the same activated carbon filters are installed, the function of the activated carbon filter disposed in front of the photocatalytic filter differs from the function of the activated carbon filter disposed behind the photocatalytic filter.

That is, the activated carbon filter disposed in front of the photocatalytic filter serves to previously adsorb gas which is superior in the competitive reaction in the photocatalytic filter in order to facilitate the decomposition of gas which falls behind in the competitive reaction in the photocatalytic filter. The activated carbon filter disposed behind the photocatalytic filter serves to adsorb gas adsorbed onto the photocatalytic filter when light is not radiated and the photocatalytic filter is not operated for a long time in order to prevent the gas from leaking to the outside of the air cleaner.

Thus, the purification efficiency of the photocatalytic filter can be further increased and odors can be prevented from being generated in the initial stage of operation of the photocatalytic filter, when the activated carbon filters are disposed in both front and rear of the photocatalytic filter, compared to when activated carbon filters, which are equal to the respective activated carbon filters disposed in the front and rear of the photocatalytic filter, are disposed only in front of the photocatalytic filter or only behind the photocatalytic filter.

Meanwhile, as described above, the less the amount of photocatalytic material loaded into the base, the less the generation of odors in the initial stage of operation of the air cleaner. On the other hand, the more the amount of photocatalytic material loaded into the base, the more increased the efficiency of the photocatalytic reaction. However, after the amount of photocatalytic material is increased to a certain level, the efficiency of the photocatalytic reaction is not increased any more.

This is because the principle of the photocatalytic reaction differs from the principle that gas is adsorbed onto the photocatalytic material. That is, the photocatalytic reaction mainly occurs only on the surface of the area to which ultraviolet light is radiated. Therefore, when the amount of photocatalytic material is present above a certain level, the area to which ultraviolet light is radiated is not increased so that the efficiency of the photocatalytic reaction is not increased. On the other hand, the gas adsorbed onto the photocatalytic material during no irradiation of ultraviolet light is not adsorbed only onto the surface of the photocatalytic material, but is also adsorbed to a predetermined depth of the material. Therefore, the more the loading amount of photocatalytic material, the more the generation of odors in the initial stage of operation of the air cleaner.

Accordingly, in order to increase the photocatalytic reaction efficiency of the photocatalytic filter while the generation of odors is reduced in the initial stage of operation of the air cleaner, it is necessary to load the photocatalytic material by an amount at the point of time in which the photocatalytic efficiency is not increased any more even when the amount of photocatalytic material is increased. For example, as seen in the graph of FIG. 24 illustrating photocatalytic reaction efficiency according to the amount of photocatalytic material loaded into the photocatalytic filter, loading 1.5 g of the photocatalytic material can minimize the generation of odors in the initial stage of operation of the air cleaner in the state in which the photocatalytic reaction efficiency is highest.

Meanwhile, the activated carbon filter includes activated carbon, and fine particles of activated carbon may be discharged to the outside of the air cleaner along the flow of air. Therefore, there is a need for a structure for preventing the above phenomenon. In particular, when at least one of the first and second activated carbon filters 70 and 75 includes granular activated carbon, the structure for preventing the activated carbon from being discharged to the outside is further required.

To this end, in the present invention, the second activated carbon filter 75 may be configured in the form of nonwoven fabric in which granular activated carbon is embedded. Alternatively, the second activated carbon filter may be configured of pulp type activated carbon. Since the nonwoven fabric or pulp may prevent particles of activated carbon from being discharged to the outside, the above filter structure may be disposed behind the second activated carbon filter or the second activated carbon filter itself may be configured in the form of nonwoven fabric or pulp for a more compact structure.

In addition, when the dust collection filter is intended to be installed in the air cleaner, the dust collection filter may be formed integrally with the second activated carbon filter, or may be disposed behind the second activated carbon filter. Of course, the use of the second activated carbon filter-combined dust collection filter may constitute a more compact air cleaner.

In accordance with the present invention, it is noted that the dust collection filter is formed integrally with the second activated carbon filter or is disposed behind the second activated carbon filter, so as to prevent the activated carbon particles of the activated carbon filter from being discharged to the outside, and the dust collection filter in which the pressure drop of air is largely generated is disposed behind the photocatalytic filter, thereby increasing the flow pressure of air coming into contact with the photocatalytic filter and increasing the contact efficiency between the air and the photocatalytic filter.

In addition, in the present invention, photocatalytic UV LEDs 57 are disposed in front of the photocatalytic filter, and thus ultraviolet light is radiated from the front of the photocatalytic filter. Thus, the photocatalytic reaction occurs from the surface of the front face of the photocatalytic filter before the pressure drop of air is generated through the photocatalytic filter, thereby increasing the decomposition efficiency of harmful gas in the photocatalytic filter. This arrangement enables the second activated carbon filter-combined dust collection filter to be disposed right behind the photocatalytic filter so as to be tight contactthereagainst. Therefore, the air cleaner may have a more compact configuration. In addition, a sterilizing UV LED 56 is installed on the UV LED substrate 55, and ultraviolet light for sterilization is radiated to the dust collection filter, which is installed right behind the photocatalytic filter, so as to sterilize microbes or virus filtered by the filter member 93. Therefore, sterilization efficiency can be excellent compared to the case in which ultraviolet light is radiated to flowing air. In addition, since the photocatalytic UV LEDs and the sterilizing UV LED are installed on a single substrate, the air cleaner has a simple structure. However, if necessary, the photocatalytic UV LEDs and the sterilizing UV LED are installed on separate substrates, and may be installed such that the ultraviolet irradiation directions from the photocatalytic UV LEDs and the sterilizing UV LED are different, for example face each other. In particular, it is harmful if ultraviolet light from the sterilizing UV LED is radiated to the human body. Therefore, it is necessary to arrange the sterilizing UV LED in consideration of the direction in which sterilization is effectively performed and the direction in which ultraviolet is not leaked to the outside.

Meanwhile, when an ultraviolet reflecting plate (not shown) is installed on the inner face of the inner housing between the photocatalytic filter and the UV LED substrate, ultraviolet light radiated to the inner face of the inner housing may be radiated again toward the photocatalytic filter, thereby further increasing deodorization and sterilization efficiency.

[Relationship Between Photocatalytic Filter and UV LED]

FIG. 14 is a perspective view illustrating the arrangement between the photocatalytic filter and the UV LED substrate. FIG. 15 is a top view illustrating the photocatalytic filter.

Referring to FIG. 14, the sterilizing UV LED 56 is installed at the central portion on the UV LED substrate 55, and three photocatalytic UV LEDs 57 are installed around the sterilizing UV LED. In particular, the photocatalytic UV LEDs 57 irradiate the photocatalytic filter 80 with ultraviolet light.

As illustrated in FIG. 15, the photocatalytic filter 80 includes the catalytic section 81 manufactured by sintering $TiO_2$ (Titanium Dioxide) to ceramic pores in the form of check lattice, and the elastic bumper 82 surrounding the side of the catalytic section.

The distance between the front face of the catalytic section and each photocatalytic UV LED 57 is expected to vary by the variation in flow property of air according to the distance between the UV LED substrate and the photocatalytic filter, and the area and irradiance of ultraviolet light reaching photocatalyst. According to its experiment, it may be seen that deodorization efficiency is highest when the length (l) of one side of the square photocatalytic filter is 5.5 cm and the distance between the light source 57 and the front face of the catalytic section 81 is 2.5 cm. In addition, it may be seen that deodorization efficiency is rapidly lowered when the distance between the light source and the front face of the catalytic section is equal to or less than 2 cm or equal to or more than 3 cm.

When the distance between the light source and the front face of the catalytic section is equal to or less than 2 cm, the area of the photocatalytic filter, which is irradiated with ultraviolet light, in the area of the photocatalytic filter is reduced, whereas photocatalytic activation efficiency is not increased any more even when the irradiance of ultraviolet light per unit area of the photocatalytic filter is increased (saturation state, see the experiments related to the irradiance of ultraviolet light to be described later in FIG. 16). In addition, when the UV LED substrate 55 is too close to the photocatalytic filter, air rarely flows in the intermediate region of the photocatalytic filter which is mainly irradiated with ultraviolet light. This is because the contact amount of air with the photocatalytic filter is small in the region in which activation is well performed.

In addition, when the distance between the light source and the front face of the catalytic section is equal to or more than 3 cm, the irradiance of ultraviolet light per unit area of the photocatalytic filter is decreased. Consequently, photocatalytic activity is lowered, and the flow of air flowing in the space between the light source and the front face of the catalytic section is stable to be a laminar flow, thereby reducing the amount of air coming into contact with the surface of the photocatalytic filter.

Meanwhile, deodorization efficiency is good when the length (l) of one side of the filter is from 4 cm to 7 cm. When the length of one side of the filter is equal to or less than 4 cm, all filters are not present in the region irradiated with ultraviolet light, resulting in a waste of ultraviolet light. On the other hand, when the length of one side of the filter is equal to or less than 7 cm, an outer filter region which is not irradiated with ultraviolet light is present, resulting in a waste of filter material.

Next, when the power is supplied to the UV LEDs 57 at a voltage equal to or less than 5 V and a current equal to or less than 200 mA, a luminescence amount is significantly reduced and UV LEDs must be added. When the voltage is 15 V or more and the current is 300 mA or more, a luminescence amount is rarely increased even when the power is increased.

Meanwhile, the inventor(s) of the present invention identifies that the deodorization performance of the photocatalytic filter vary according to the shape of the lattice formed in the catalytic section 81, the spacing distance (g) of each cell 83, the frame thickness (t) of the lattice, the length (l) of one side of the catalytic section, the number (n) of cells of the catalytic section, the height (h) of the catalytic section, the flow direction (forward direction, reverse direction) of air, the sintering temperature and time of the catalytic section, the peak wavelength of the photocatalytic UV LED 57, and the irradiance of ultraviolet light radiated to the front face of the catalytic section.

FIG. 16 is a graph illustrating a decomposition rate of acetaldehyde according to the irradiance of ultraviolet light reaching the front face of the photocatalytic filter.

First, the variation in deodorization performance of the photocatalytic filter according to the irradiance of ultraviolet light radiated to the front face of the catalytic section is repeatedly measured. As the result of measurement, it is seen that the deodorization efficiency of photocatalyst is increased as the irradiance of ultraviolet light is increased until the irradiance of ultraviolet light per unit area of the photocatalytic surface is 14.67 $mW/cm^2$. However, it is seen that the deodorization efficiency is not increased even though the irradiance of ultraviolet light is increased. In particular, this tendency is consistent regardless of the spacing distance (g) of each cell 83, the frame thickness (t) of the lattice, the length (l) of one side of the catalytic section, the number (n) of cells of the catalytic section, the height (h) of the catalytic section, and the sintering temperature and time of the catalytic section.

In addition, according to the repetitive result of experiments, when the irradiance of ultraviolet light per unit area of the photocatalytic surface is less than 10 $mW/cm^2$, the deodorization efficiency by the photocatalytic reaction is rapidly decreased. When the irradiance of ultraviolet light per unit area of the photocatalytic surface is more than 20 $mW/cm^2$, the deodorization efficiency by the photocatalytic activation is rarely increased while only electric energy is consumed to increase the irradiance of ultraviolet light.

FIG. 17 is a graph illustrating the ultraviolet absorbance of the photocatalytic filter according to ultraviolet wavelengths. FIG. 18 is a graph illustrating a removal rate of acetaldehyde according to ultraviolet wavelengths.

As illustrated in FIG. 17, it may be seen that the ultraviolet absorbance of the $TiO_2$ photocatalytic filter according to ultraviolet wavelengths is good in the wavelength band of about 270 nm, and the ultraviolet absorbance is linearly reduced toward the wavelength band of 400 nm. However, it may be seen that, when the UV LED is actually used, the UV LED has a peak wavelength of 365 nm which exhibits excellent photocatalytic efficiency. This is caused by the luminous efficiency of the UV LED. Since the luminescence amount of the UV LED is rapidly reduced as the UV LED has a shorter peak wavelength, a large number of UV LEDs must be used in order to adjust the irradiance of ultraviolet light required for the surface of the photocatalytic filter using the UV LED having a shorter peak wavelength. However, there is a problem in that the substrate has a limited size for the flow of air and costs are increased. As the result of experiments considering the above problem, it may be identified that the deodorization efficiency by the photocatalytic filter is rapidly lowered when an UV LED having a peak wavelength equal to or less than 340 nm is used.

In addition, when an UV LED having a peak wavelength equal to or more than 380 nm is used, the ultraviolet absorbance of the photocatalyst is significantly decreased, and there is a little between the UV LED and the existing black light which is commonly used as a ultraviolet light lamp. Therefore, the use of the UV LED is meaningless.

As the result of experiments, it may be identified that the deodorization performance by the photocatalytic filter is highest when an UV LED having a peak wavelength which is from 360 nm to 370 nm is used.

FIG. 19 is a graph illustrating a difference in deodorization rate of acetaldehyde according to the height (h) of the photocatalytic filter. FIG. 20 is a graph illustrating a difference in deodorization rate of acetic acid according to the height (h) of the photocatalytic filter.

As the result of experiments, in the photocatalytic filter illustrated in FIG. 15, the area of the photocatalytic surface in the front face of the photocatalytic filter increased by the frame thickness (t) thereof rarely affect to the deodorization efficiency of the photocatalytic filter, but the height (depth) of the photocatalytic filter affects to the area of the inner wall in the air flow path, to thereby have a direct effect on the contact area with air.

Thus, it may be identified that the deodorization efficiency of the photocatalytic filter is highest when the height of the filter is 5 to 10 mm. In addition, when the height is equal to or less than 2 mm, it is difficult to use the photocatalytic filter since the strength thereof is weak. When the height is equal to or more than 15 mm, only air resistance is increased, and ultraviolet light does not reach the photocatalytic filter or the irradiance thereof is significantly decreased. As a result, only costs are increased while the deodorization efficiency is not increased.

In addition, it may be identified that, when the inner spacing distance of the cell 83 is 2 mm, air resistance is not increased, and shaded area caused by the shape of the filter itself blocking ultraviolet light radiated into the filter is not so much that each cell irradiated with ultraviolet light has a proper inner area. When the inner spacing distance is equal to or less than 1 mm, air resistance is increased, and the amount of ultraviolet light reaching the inner wall is reduced, thereby deteriorating deodorization efficiency. When the inner spacing distance is equal to or more than 4 mm, the density of the cell is low and the area of the inner wall is reduced, thereby deteriorating deodorization efficiency.

In terms of the density of the cell, when the density of the cell is less than 30 cell/inch$^2$, the inner spacing distance is 4 mm or more, and the area of the inner wall is reduced, thereby deteriorating deodorization efficiency. When the density of the cell is equal to or more than 260 cell/inch$^2$, the inner spacing distance is 1 mm or less, air resistance is increased, and the amount of ultraviolet light reaching the inner wall is reduced, thereby deteriorating deodorization efficiency. When the density of the cell is about 100 cell/inch$^2$, air resistance is not increased, and ultraviolet light radiated into the filter is not blocked so much by the shape of the filter itself that shading is not nearly generated and deodorization efficiency is the highest.

Next, as the result of experiment on the frame thickness (t), when the thickness is equal to or less than 0.3 mm, a $TiO_2$ layer is significantly thinned, and photocatalytic efficiency and strength is lowered. When the thickness is equal to or more than 1.2 mm, photocatalytic efficiency is not increased while only material costs are increased. When the thickness is 0.6 mm, photocatalytic efficiency is the highest.

FIG. 21 is a graph illustrating deodorization performance for each sintering temperature of the photocatalytic filter when 2 g of $TiO_2$ is sintered for one hour. FIG. 22 is a graph illustrating deodorization performance for each sintering temperature of the photocatalytic filter when 2.5 g of $TiO_2$ is sintered for one hour. FIG. 23 is a graph illustrating deodorization performance for each sintering temperature of photocatalytic filters manufactured by sintering 2.5 g of $TiO_2$ at a sintering temperature of 400° C. for different times.

Referring to FIGS. 21 to 23, it may be identified that the deodorization performance is good when the sintering temperature is 350 to 450° C., and there is no problem about the deodorization performance of the photocatalytic filter when the sintering time is 1 to 2 hours. Accordingly, when considering the variation in temperature, the sintering may not be completed at a temperature of 400° C. for a sintering time less than one hour. Since the deodorization performance of the photocatalytic filter is deteriorated when the sintering time is too long, the sintering time is preferably 1 to 2 hours.

Various embodiments have been described in the best mode for carrying out the invention. Although the present invention has been described with respect to the illustrative embodiments, it will be apparent to those skilled in the art that various variations and modifications may be made without departing from the spirit and scope of the invention as defined in the following claims.

INDUSTRIAL APPLICABILITY

It is apparent that the present invention has industrial applicability.

The invention claimed is:

1. An air cleaner comprising:
    a body having a first housing formed in a lower part of the body and a second housing formed in an upper part of the body;
    an air inlet port formed in the first housing and positioned to introduce air into the body,
    an air flow path positioned to cause the introduced air to flow from the first housing into the second housing along the air flow path;
    a filter disposed in the air inlet port and configured to control air quality of the introduced air;
    a UV LED (ultraviolet light emitting device) disposed in the air flow path and configured to radiate, towards air moving from the lower part to the upper part, ultraviolet light having a sterilization wavelength; and
    an outlet disposed in an upper portion of the second housing and configured to discharge air to an outside,
    wherein the air cleaner further comprises a duct disposed between the filter and the outlet, the duct having a flat sidewall and a curved sidewall that is curved such that a cross-sectional area of the duct gradually enlarges along the air flow path.

2. The air cleaner of claim 1, wherein the filter is detachably provided in the air inlet port.

3. The air cleaner of claim 1, further comprising an inlet grate formed in the first housing and serving as a passage for air to enter into the body.

4. The air cleaner of claim 1, further comprising a photocatalytic filter disposed above the UV LED along a flow direction of the air flow.

5. The air cleaner according to claim 1, further comprising:
    a fan installed in the first housing and operating to facilitate the introduction of air into the air inlet port.

6. The air cleaner according to claim 1, further comprising a duct formed between the UV LED and the outlet in order to guide a flow of air to the outlet and having a curved shape.

7. The air cleaner according to claim 6, wherein:
    the UV LED is installed at an upper portion of the duct while being spaced apart therefrom; and
    the UV LED is disposed on a substrate inclined with respect to a surface of the body.

8. The air cleaner according to claim 1, further comprising an ultraviolet emission prevention plate installed between the UV LED and the outlet in order to prevent ultraviolet light from being directly radiated to the outside through the outlet section.

9. The air cleaner according to claim 1, wherein the first housing has a smaller diameter than the second housing.

10. The air cleaner according to claim 1, wherein the filter includes a carbon filter.

11. The air cleaner according to claim 1, wherein the air inlet port is formed with a pair of parallel stepped members; and the filter comprises a housing having a width and disposed between the pair of the stepped members.

12. The air cleaner according to claim 1 further comprising a flow guide for guiding air to and formed in the body above the air inlet port.

13. The air cleaner according to claim 1, wherein the filter comprises a housing formed with a pre-filter surface (72), and including activated carbon received in the housing.

14. An air cleaner comprising:
a body having a first housing formed in a lower part of the body and a second housing formed in an upper part of the body;
an air inlet port formed in the first housing and operating to introduce air into the body, wherein the introduced air flows along an upward air flow path from the lower part to the upper part of the body;
a UV LED (ultraviolet light emitting device) disposed in the air flow path and configured to radiate ultraviolet light having a sterilization wavelength toward air moving from the lower part to the upper part;
a filter disposed above the UV LED and configured to control air quality of air flowing through the second housing;
a fan disposed below the UV LED; and wherein the air cleaner further comprises a duct disposed in an upper portion of the fan, the duct having a flat sidewall and a curved sidewall that is curved such that a cross-sectional area of the duct gradually enlarges along the air flow path.

15. The air cleaner of claim 14, further comprising an additional filter disposed in the air inlet port and configured to control air quality of the introduced air.

16. The air cleaner of claim 14, wherein the filter includes a photocatalytic filter or a dust collection filter, or both of the photocatalytic filter and the dust collection filter.

17. The air cleaner of claim 14, further comprising a duct formed between the UV LED and the outlet in order to guide a flow of air to the outlet and having a curved shape.

18. The air cleaner of claim 14, wherein the first housing has a smaller diameter than the second housing.

19. The air cleaner according to claim 14, wherein the UV LED radiates ultraviolet light having a sterilization wavelength in a same direction as an ultraviolet irradiation direction in which ultraviolet light is irradiated from the filter.

20. The air cleaner according to claim 14, further comprising a dust collection filter installed to a rear face of the filter.

21. The air cleaner according to claim 14, further comprising a dust collection filter installed between the UV LED and the filter along a flow direction of air.

* * * * *